United States Patent
Webb, III et al.

(10) Patent No.: US 8,825,786 B1
(45) Date of Patent: Sep. 2, 2014

(54) SYSTEM FOR EXCHANGING MEDICAL INFORMATION

(71) Applicants: William Baxter Webb, III, Nashville, TN (US); Christopher Rathermel, Nashville, TN (US)

(72) Inventors: William Baxter Webb, III, Nashville, TN (US); Christopher Rathermel, Nashville, TN (US)

( * ) Notice: Subject to any disclaimer, the term of this patent is extended or adjusted under 35 U.S.C. 154(b) by 0 days.

(21) Appl. No.: 14/096,062

(22) Filed: Dec. 4, 2013

Related U.S. Application Data

(60) Provisional application No. 61/872,238, filed on Aug. 30, 2013.

(51) Int. Cl.
  *G06F 15/16* (2006.01)
  *G06F 19/00* (2011.01)
(52) U.S. Cl.
  CPC .................................... *G06F 19/322* (2013.01)
  USPC ............... 709/206; 600/300; 705/2; 370/310; 370/460
(58) Field of Classification Search
  None
  See application file for complete search history.

(56) References Cited

U.S. PATENT DOCUMENTS

| | | | |
|---|---|---|---|
| 5,958,005 A | 9/1999 | Thorne et al. | |
| 6,721,784 B1 | 4/2004 | Leonard et al. | |
| 8,345,836 B2 | 1/2013 | Katis et al. | |
| 2004/0059600 A1* | 3/2004 | Ball et al. | 705/2 |
| 2006/0253894 A1* | 11/2006 | Bookman et al. | 726/2 |
| 2007/0064703 A1 | 3/2007 | Hernandez et al. | |
| 2007/0130363 A1 | 6/2007 | Barros | |
| 2008/0294586 A1 | 11/2008 | Lim | |
| 2010/0161743 A1 | 6/2010 | Krishnamurthi et al. | |
| 2011/0202598 A1 | 8/2011 | Evans et al. | |
| 2012/0179550 A1* | 7/2012 | Vieri | 705/14.64 |

* cited by examiner

*Primary Examiner* — Valerie Lubin
(74) *Attorney, Agent, or Firm* — Waddey Patterson; Gary L. Montle

(57) ABSTRACT

A server-based system enables exchange of medical messages between users, monitors for a probability of communications breakdown likely to result in medical error, and instigates corrective actions to prevent communications breakdown from occurring. Monitoring may include whether a user has read or acted upon a message received within a specified timeframe and whether a user has specified routing preferences for delivering a message to a user better suited to read or act on the message. Corrective actions include the determination of and routing of messages to an optimal recipient and the generation of alerts to subsequent users where a message has not been read or acted upon within a specified timeframe.

20 Claims, 14 Drawing Sheets

FIG. 10

FIG. 11

SYSTEM FOR EXCHANGING MEDICAL INFORMATION

CROSS-REFERENCES TO RELATED APPLICATIONS

This application claims benefit of the following patent application(s) which is/are hereby incorporated by reference: U.S. Provisional Application No. 61/872,238, filed Aug. 30, 2013.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF THE INVENTION

The present invention relates generally to a system for exchanging medical information. More particularly, this invention relates to a server-based system which effectively exchanges patient-related messages between healthcare providers, prioritizes messages based on message content, routes messages to optimal recipients based on messaging forwarding algorithms, monitors the read status of messages after they have been sent, alerts healthcare providers when a high priority message has not been read, and performs message analysis to determine if a breakdown in communication between healthcare providers is likely to occur.

Communications breakdowns are one of the greatest causes of fatal and nonfatal medical errors in the United States. An estimated 200,000 fatal medical errors occur each year, 70% of which are attributable to a breakdown in communications between healthcare providers. Many of these communications breakdowns are systematic in nature; one in seven messages is sent to the wrong clinician, and thirty percent of all messages go unanswered by the recipient. Furthermore, paging can interrupt clinician workflows between ten and twenty times per hour, causing clinicians to spend more time processing communications than performing direct patient care. As such, healthcare providers often fear interrupting physicians with pages even when a problem is occurring.

As a result, messages will often go undelivered, and many that are delivered are ignored because the healthcare provider is not in a position to read or act upon the message. Forwarding the message to a healthcare provider who is in a position to read or act upon the message takes additional time and often requires contextual information not available to the sender or receiver of the message. Therefore, critical messages pertaining to a patient's healthcare often get lost amid the din of digital communications, often resulting in fatal medical errors.

BRIEF SUMMARY OF THE INVENTION

In accordance with one aspect of the present invention, a web-based system acts on behalf of the user (healthcare provider) to exchange patient-related messages between healthcare providers, prioritize messages based on message content, route messages to optimal recipients based on messaging forwarding algorithms, monitor the read status of messages after they have been sent, alert healthcare providers when a high priority message has not been read, and perform message analysis to determine if a breakdown in communication between healthcare providers is likely to occur.

In an aspect of the system, messages sent between healthcare providers are analyzed for a likelihood of medical error resulting from a breakdown in communications. In another aspect of the system, routing of messages may be modified from an intended recipient to an optimal recipient to prevent a likelihood of medical error resulting from a breakdown in communications.

In an embodiment, a server-based system for medical messaging enables the exchange of messages between users. The system comprises host system effective to process the delivery and routing of messages, a messaging database effective to store a plurality of messages associated with patients and healthcare providers, and an algorithm database effective to store a plurality of algorithms for processing said messages. The system enables users to view and compose messages associated with a medical patient. The system enables users to access messages via an endpoint device whereby the system displays message information associated with the user through a user interface. The system transmits new messages composed upon the endpoint device to the host system, determines the optimal recipient for the message according to one or more algorithms stored in the algorithm database, stores the message on the message database, and notifies the optimal recipient of the message. The system additionally monitors the message status to ensure a recipient has viewed or acted upon the message and generates additional notifications to the optimal recipient or other users where a message has gone unviewed or without requisite action.

BRIEF DESCRIPTION OF THE SEVERAL VIEWS OF THE DRAWINGS

FIG. 10 is a modified screen shot representing a second exemplary graphical user interface field according to the present invention.

FIG. 11 is a modified screen shot representing a third exemplary graphical user interface field according to the present invention.

DETAILED DESCRIPTION OF THE INVENTION

Figure 1A:
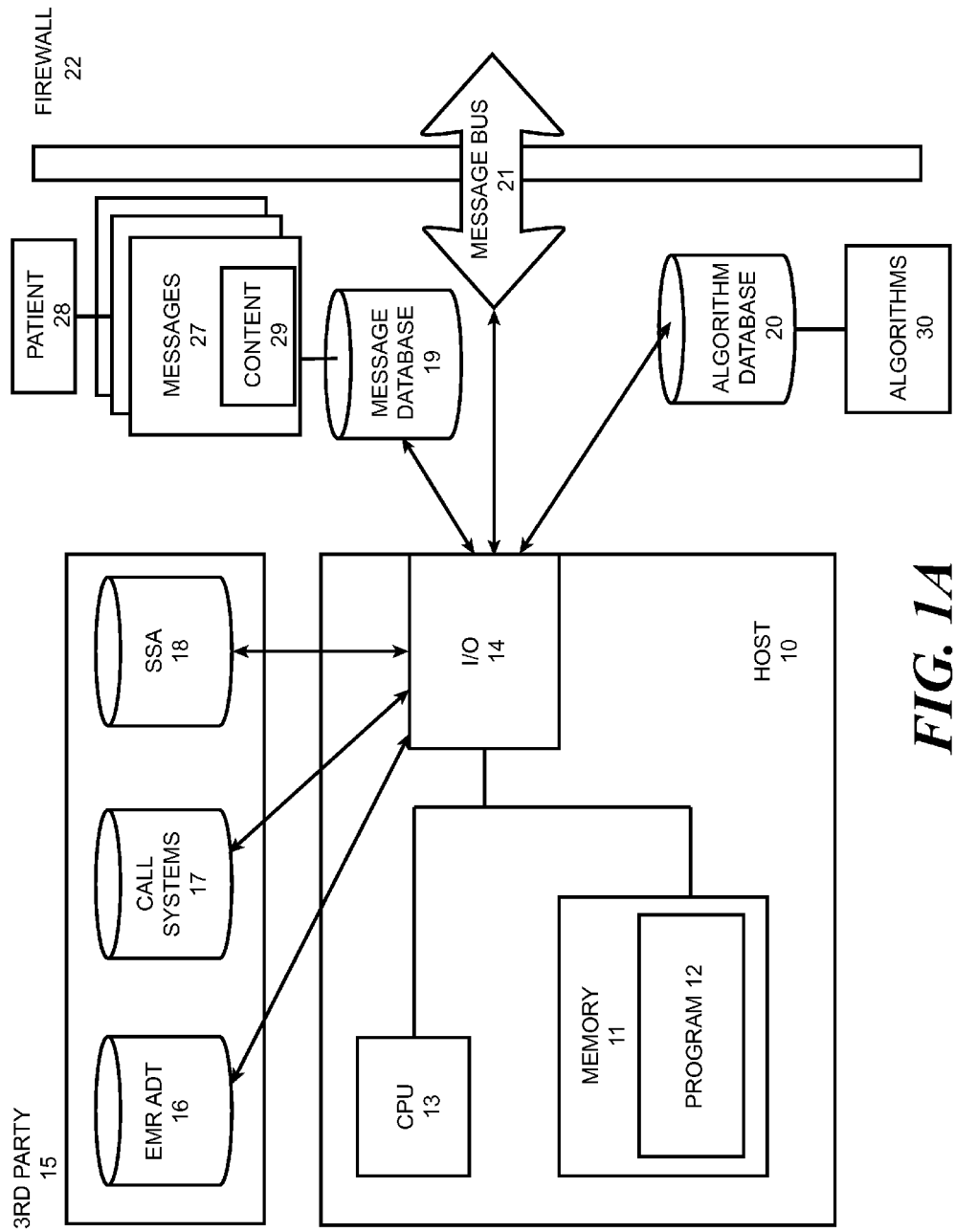
FIG. 1A is a block diagram representing an embodiment of a system according to the present invention.

Referring generally to FIGS. 1-12, various embodiments of a system for exchanging medical information may be further described herein. Briefly stated, a messaging system in accordance with the present disclosure exchanges messages between healthcare providers and employs message routing and post-delivery message monitoring effective to reduce the likelihood of communication breakdown. The message may be routed to an optimal recipient that is different than the intended recipient based on the intended recipient's routing preferences. The system may monitor the post-delivery status of the message, including whether the message has been read or if a recipient has responded to the message, and determine that an alert should be generated to prevent the occurrence of a communication breakdown that may result in medical error.

Where the various figures may describe embodiments sharing various common elements and features with other embodiments, similar elements and features are given the same reference numerals and redundant description thereof may be omitted below.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may. Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

Depending on the embodiment, certain acts, events, or functions of any of the algorithms described herein can be performed in a different sequence, can be added, merged, or left out altogether (e.g., not all described acts or events are necessary for the practice of the algorithm). Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable medium known in the art. An exemplary computer-readable medium can be coupled to the processor such that the processor can read information from, and write information to, the memory/storage medium. In the alternative, the medium can be integral to the processor. The processor and the medium can reside in an ASIC. The ASIC can reside in a user terminal. In the alternative, the processor and the medium can reside as discrete components in a user terminal.

The term "user interface" as used herein may unless otherwise stated include any input-output module with respect to the hosted server including but not limited to web portals, such as individual web pages or those collectively defining a hosted website, mobile desktop applications, telephony interfaces such as interactive voice response (IVR), and the like. Such interfaces may in a broader sense include pop-ups or links to third party websites for the purpose of further accessing and/or integrating associated materials, data or program functions via the hosted system and in accordance with methods of the present invention.

The term "web-based network structure" as used herein may, unless otherwise stated, refer generally to a platform effective to implement web-transitory functions, whether browser-based or otherwise. In other embodiments, the host system may within the scope of the present invention include other computer-implemented platforms and networks known to those of skill in the art which are not web-based.

The term "communications network" as used herein with respect to data communication between two or more parties or otherwise between communications network interfaces associated with two or more parties may therefore refer to any one of, or a combination of any two or more of, telecommunications networks (whether wired, wireless, cellular or the like), a global network such as the Internet, local networks, network links, Internet Service Providers (ISP's), and intermediate communication interfaces.

The term "healthcare provider" as used herein may refer to any person or group of persons who provide medical services associated with a patient including but not limited to clinicians, physicians, dentists, radiologists, optometrists, chiropractors, pharmacists, physician assistants, nurses, dieticians, therapists, psychologists, emergency medical technicians, and paramedics.

The term "user" as used herein may include for example individual healthcare providers, a group of healthcare providers, a healthcare patient/consumer/recipient/caregiver or may refer instead to any other entity that may require access to the messaging system.

Referring first to FIG. 1, various embodiments of the host system 10 as disclosed herein include a computer-readable medium 11 having program module 12 with processor-executable instructions embodied thereon. The medium 11 may generally be effective to store data accessible to a processor 13 to which the medium 11 may be operatively linked. When the medium 11 is operatively coupled to a processor 13 the instructions may be executed by the processor 13 to perform various functions recited herein.

Figure 1B:
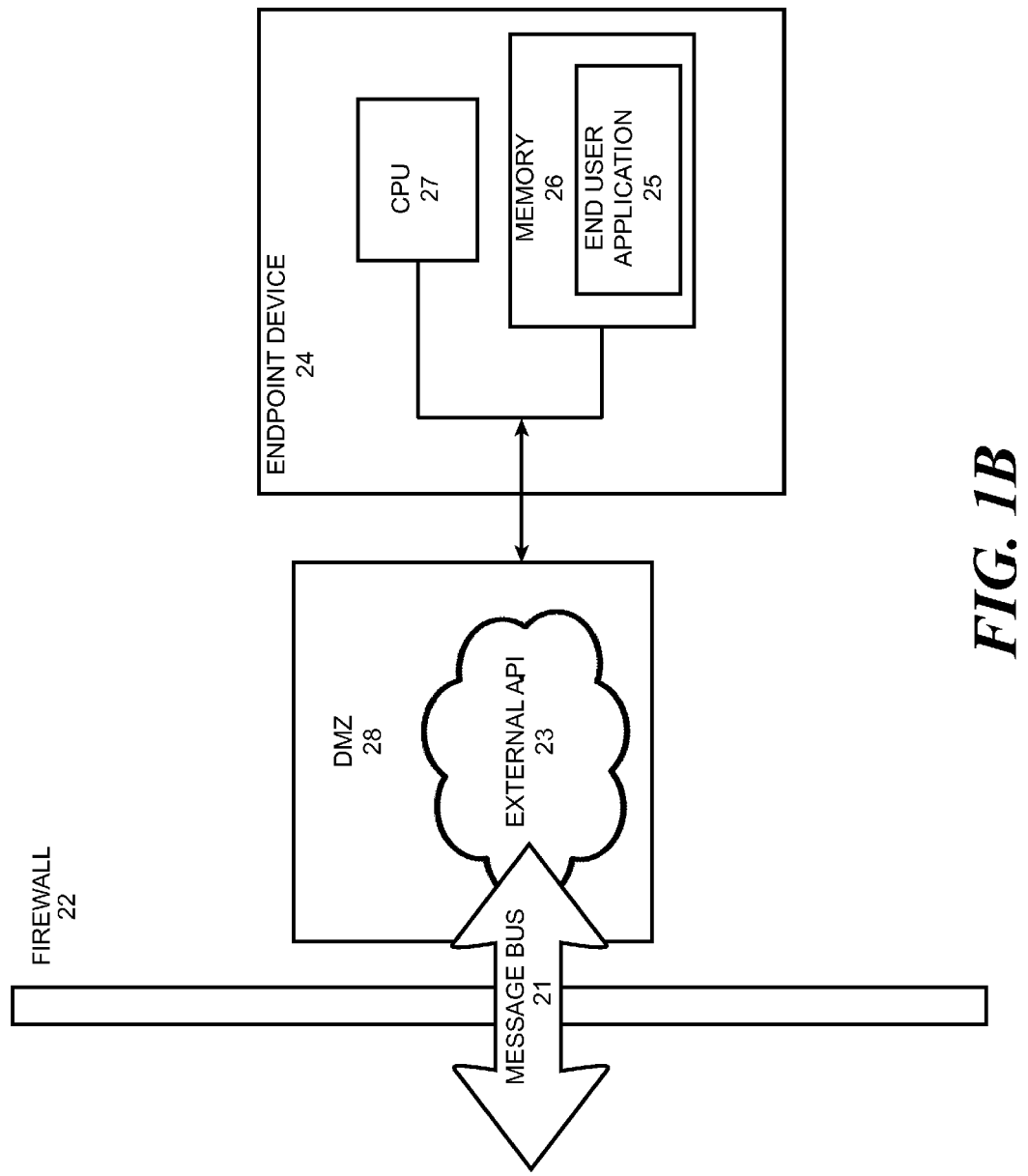
FIG. 1B is a block diagram representing an embodiment of a second portion of a system according to the present invention.

In an embodiment as shown in FIGS. 1A and 1B, a host system 10 includes the medium 11 operatively connected to a processor 13 effective to execute the instructions stored upon the program module 12. The medium 11 and processor 13 may be communicatively coupled to one or more input and/or output (I/O) devices 14. The I/O device 14 can include devices, for instance, but not limited to a modem for accessing another device, system, or network; a transceiver, a telephonic interface, a bridge, or a router. The I/O device 14 may be communicatively connected to one or more databases including a message database 19 effective to store one or more messages 27 associated with a patient 28, the messages comprising content 29; and an algorithm database 20 effective to store one or more algorithms 30 for processing the handling and routing of messages 27 and/or message content 29. The I/O device 14 may further be communicatively connected to third party databases 15 which may include an Admission, Discharge and Transfer System of an Emergency Medical Records database 16, one or more Call Systems databases 17, and a Single Sign-On Authentication database 18.

The host system 10 may be communicatively connected to one or more endpoint devices 24 by means of a message bus 21. The message bus can include hardware or software bus network structure connections between the host system 10 and the endpoint devices 24 and may be effective to exchange data across a firewall 22 that isolates the host system 10. The message bus may further facilitate a secure connection between the endpoint device 24 and the host system 10, the secure connection including but not limited to secure socket layer (SSL) connection. The endpoint device 24 may include a second non-transitory processor-readable memory medium (hereinafter referred to as the endpoint memory) 26 having an end user application program 25 with processor-readable instructions embodied thereon. The endpoint memory 26 may generally be effective to store data accessible to a second endpoint device processor 27 to which the endpoint memory 26 may be operatively linked. When the endpoint memory 26 is operatively coupled to the second processor 27 the instructions may be executed by the second processor 27 to receive data from the message bus 21. The instructions may be executed by the second processor 27 according to instructions provided from an external API 23 that exists outside the firewall 22 in relation to the host system 10. The external API 23 may exist on a demilitarized host 28 to which the endpoint device 24 is communicatively connected. The demilitarized host 28 may include one or more logical servers, physical computer servers, or combinations thereof. The endpoint device may be effective to provide data received from the message bus 21 and through the external API 23 to an end user application 25 stored upon the endpoint memory 26.

Figure 2A:
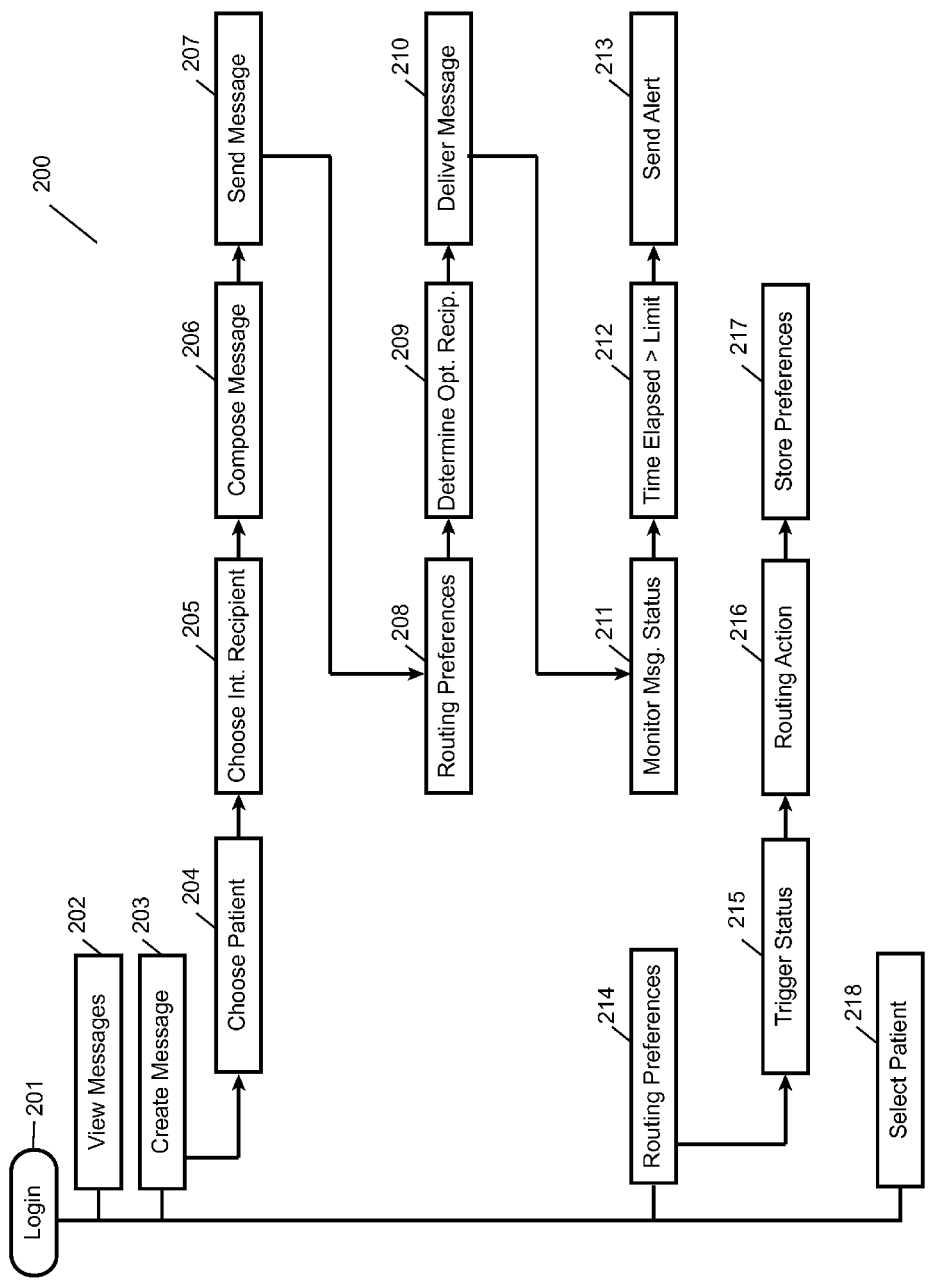
FIG. 2A is a flowchart representing on embodiment of a method according to the present invention.
Figure 2B:
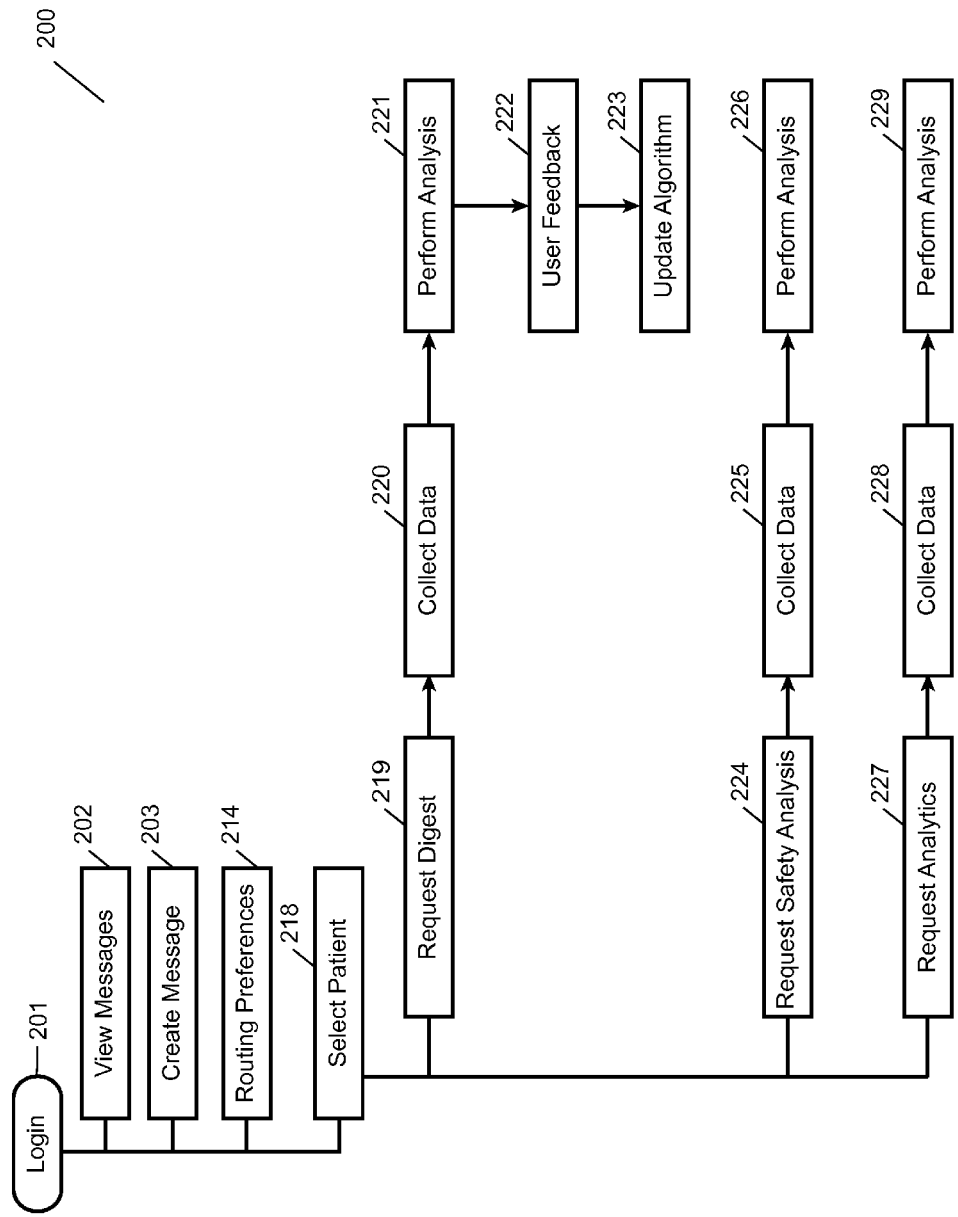
FIG. 2B is a flowchart representing another embodiment of a method according to the present invention.

An embodiment of a messaging method 200 may be described in association with the host system represented in FIGS. 1A and 1B herein with respect to FIG. 2A. The method 200 begins at step 201 by a user successfully logging into the host system 10. In an embodiment, the user successfully logs in by establishing a secure connection between an endpoint device 24 and the host system 10, sending login credentials to the host system 10, and having the host system 10 authenticate the login credentials and grant access to the securely connected endpoint device 24.

Upon establishing a successful login, the host system 10 may present the user with several options for interacting with the messaging system. In various embodiments, the user may choose to view one or more messages associated with the user as further defined in step 202. If the user chooses to view messages, the host system 10 may provide a list of messages with which the user is associated. The messages may be associated to the user by being associated with patients with which the user is associated. In various embodiments, some or all of the associated messages may be presented along with their content through a graphical user interface as rendered by the end user application 25 of the endpoint device 24. In certain embodiments, messages may be displayed as a truncated list with a summary of message content including the name of the patient with whom the message is associated, the date and time at which the message was sent, the title subject of the message, the priority of the message, and whether or not the message has been read.

A user may choose to create a message, whereupon the method 200 proceeds to step 203 by presenting the user with a message creation function. In certain embodiments, the host system may present the message creation function through a graphical user interface as rendered by the end user application 25 of the endpoint device 24. The method 200 then proceeds to step 204 by determining a patient of the user's choice with whom to associate the new message. In various embodiments, a user may be presented with a list of associated patients. The host system 10 may determine the list of associated patients by requesting a list of patients from the electronic medical records system 16 and the message database 19. The host system 10 may combine the list of patients determined from the electronic medical records system 16 and the message database 19 into a unified, non-redundant list to display to the user. This unified, non-redundant list may be streamed across the message bus 21 to the user's endpoint device 24 in a transitory manner so that the list may not be retained upon the endpoint device following termination of the login session as described in step 201 above. In an alternative embodiment, the user may choose a patient not initially associated with the user from a list of all patients associated with the electronic medical records system 16 and message database 19.

In one embodiment, the electronic medical records system may store information regarding which users have accessed patient data through the host system 10 in accordance with the method 200 as necessary to create a HIPAA audit log. The host system 10 may therefore forward access information to the electronic medical records system 16.

Upon determination of a selected patient, the method 200 then proceeds to step 205 by determining one or more recipients for the new message. In various embodiments, the one or more recipients may be chosen from a list of healthcare providers associated with the selected patient. The host system 10 may determine the list of associated recipients by requesting a list of healthcare providers associated with the selected patient from the electronic medical records system 16, the call systems database 17, and the message database 19. The host system 10 may combine the list of healthcare providers determined from the electronic medical records system 16, the call systems database 17, and the message database 19 into a unified, non-redundant list to display to the user. This unified, non-redundant list may be streamed across the message bus 21 to the user's endpoint device 24 in a transitory manner so that the list may not be retained upon the endpoint device following termination of the login session as described in step 201 above. In an alternative embodiment, a user may choose one or more recipients not initially associated with the patient from a list of all healthcare providers associated with the host system 10 and call systems database 17.

The user may then compose the message by populating the message with message content (step 206). In various embodiments, the user may compose a message with content consisting of alphanumeric text characters. In another embodiment, the user may compose a message with content consisting of electronically stored audio, imagery, or video. In certain embodiments, the message content may include a message title subject, a message body of content, and a message priority. The message priority may be selected from a list of predetermined priority levels. This selection may be made by the user or alternatively may be automatically determined by the host system 10 from the message content according to a natural language processing algorithm stored on the algorithm database 30. In an embodiment, the message composition may occur within the end user application 25 on the user's endpoint device. The message content may be stored for purposes of composition on an external API 23 of a demilitarized host 28 so that none of the message content persists in the endpoint memory 26 following termination of the login session as described in step 201 above.

Upon completion of message composition, the method 200 then proceeds to step 207 wherein the message is sent by the user. In an embodiment, the message may be sent according to instructions sent from the user's endpoint device 24 across a message bus 21 to the host system 10. The host system 10 may write the message 27 and message content 29 to the message database 19.

The method 200 continues in step 208 by determining whether any associated routing preferences. In various embodiments, healthcare providers may have associated routing preferences that determine optimal routing procedures according to various criteria. Criteria may include date and/or time that the message has been sent, the geospatial location of the healthcare provider or the healthcare provider's endpoint device, the presence or absence of certain wireless communications networks visible to the healthcare provider's endpoint device, and the priority of the message. For example, a healthcare provider may have routing preferences defined for when the healthcare provider is not on site at the hospital to route messages to a healthcare provider on call. In another example, a healthcare provider may have routing preferences defined to receive messages of high priority during non-business hours but to route messages of low priority to an on-call physician or nurse. In an embodiment, a healthcare provider's routing preferences may be defined by the healthcare provider. In an alternative embodiment, the healthcare provider's routing preferences may be automatically determined by the host system 10 according to one or more algorithms 30 stored on the algorithms database 20.

Upon determination of the recipient's routing preferences, the method 200 proceeds to step 209 by determining the optimal recipient for the message. In various embodiments where a recipient has routing preferences defined, the host system 10 determines the optimum recipient for the message according to the selected recipient's routing preferences. The routing preferences may be stored as one or more algorithms 30 in the algorithm database 20, the call systems database 17, or both. In an embodiment wherein the recipient does not have routing preferences defined, the host system 10 may determine that the selected recipient is the optimal recipient for the message.

The method 200 continues to step 210 by sending the message to the optimal recipient as determined prior in step 209. In various embodiments, the host system 10 logically associates the message stored upon the message database 19 with the optimal recipient. The host system may send a notification to the optimal recipient regarding the existence of the message on the message database 19. In an embodiment, the message content is retained on the message server 19 and is streamed by the host system 10 across a message bus 21 to an external API 23 to which the optimal recipient's endpoint device 24 connects. The host system 10 may stream content in this manner in a transitory state so that none of the message content persists in the endpoint memory 26 following termination of the login session as described in step 201 above. Notification may occur by direct notification through the system or by push notification through a third-party system. Examples of third-party push notification systems include but are not limited to Apple Push Notification, Android Push Notification, Parse, and Urban Airship.

The method 200 then proceeds to step 211 wherein the host system 10 monitors the time elapsed since the message has been sent and the message status. In various embodiments the message status may include whether the message has been seen by the optimal recipient and whether the optimal recipient has responded to the message. The host system 10 may additionally determine the priority of the message and one or more time limits associated with the message priority for which the message can go unread or without recipient response. For example, a high priority message may have a time limit specifying that the message must be read within 2 minutes since the message was initially sent and must be responded to within 5 minutes since the message was initially sent, whereas a low priority message may have a time limit specifying that the message must be read within 24 hours since the message was initially sent and may not have a time limit specifying the time by which the recipient must respond to the message. In an embodiment, the one or more time limits are customizable.

The host system 10 compares the message status and the time elapsed since the message has been sent to the one or more time limits associated with the message priority (step 212). In various embodiments, if the time elapsed exceeds the time limit for the message status, the host system 10 will generate and send an alert (step 213). The alert may be generated according to one or more algorithms 30 stored in the algorithm database 20. The algorithms 30 may specify to generate and send an e-mail to a specific user, place an automated phone call to a specific user, or send a notification to a specific user according to the various embodiments described in step 210. Alternatively, if the time elapsed has not exceeded the time limit or if no time limit exists for the determined message status, the host system 10 may cease the monitoring activities of steps 210 and 211 for that message.

A user successfully logged in according to step 201 may choose to specify or update his or her routing preferences, wherein the method 200 proceeds to step 214. In various embodiments, the host system 10 may present routing preferences update function through a graphical user interface as rendered by the end user application 25 of the endpoint device 24. The user may choose a trigger status (step 215) from a list of pre-defined trigger statuses, the trigger status determining when the routing preference should be effective to the host system 10 upon the routing of messages as specified above in step 208. The trigger status may include criteria such as date and/or time that an incoming message has been sent, the geospatial location of the user or the user's endpoint device, the presence or absence of certain wireless communications networks visible to the user's provider's endpoint device, and the priority of an incoming message.

After a user has selected a trigger status, the method 200 continues to step 215 by prompting a user for a subsequent routing action associated with the trigger status. The user may choose a routing action from a list of pre-defined routing actions. For example, a user may choose to route messages received during a particular trigger status to a specific healthcare provider. Alternatively, a user may choose a general routing function without a predefined recipient, whereby the host system 10 will determine the specific recipient at the time that the message is sent to the user. For example, a user may choose to route messages to an attending physician on call, whereupon the host system 10 will determine at the time the message is sent to the user which specific healthcare provider is the physician on call by querying the call systems database 17.

The method 200 then proceeds to step 216 by committing and storing the updated preferences. In various embodiments, when the user specifies for the routing preference to be saved, the routing preference is translated into an algorithm to be stored upon the algorithm database 30 to be referenced by the host system 10 such as during step 208. In one embodiment, the algorithm may be sent from the endpoint device 24 through the message bus 21 to the host system 10 to be stored by the host system 10 on the algorithm database 30. In an alternative embodiment, the algorithm may be determined, constructed, and stored onto the algorithm database 20 by the host system 10 from data received by the endpoint device 24.

A user successfully logged in according to step 201 may choose to perform patient analysis functions for a particular, wherein the method 200 proceeds to step 218. In various embodiments, the host system 10 may present the patient analysis functions through a graphical user interface as rendered by the end user application 25 of the endpoint device 24. In various embodiments, the user may pre-select a patient for which the host system 10 will perform certain analytics. In alternative embodiments, such as may be represented for example in FIG. 2B, the user may choose the particular analytics function (steps 219, 224, 227) prior to determining the patient upon which the analytics function should be performed. In another embodiment, the host system 10 may update the call systems database 17 with the updated routing preferences.

If a user requests a message digest for a patient, the method 200 proceeds to step 219 by forwarding the digest request from the user's endpoint device 24 to the host system. The host system 10 may load from the algorithm database 20 a digest algorithm that instructs the host system 10 in performing a message digest search.

The method 200 proceeds to step 220 wherein the host system 10 collects messages 27 and message content 29 from the message database 19. In various embodiments, the host system 10 processes only messages 27 and message content 29 associated with the selected patient. The method 200 then proceeds to step 221 wherein the host system 10 performs analysis on the collected messages according to the message digest algorithm to determine the relative importance of the message. In various embodiments, the algorithm dictates to the host system 10 to process message characteristics including message priority, the time at which the message was sent, the recipients of the message, and the message content. The host system 10 applies the message algorithm to make a Boolean determination of the message importance according to the message characteristics. The host system 10 may therefore flag a message as important or not flag a message as important. In various embodiments, the host system 10 will output a summary list of messages to the user. In an embodiment, the host system 10 may stream the summary list of messages across the data bus 21 to the endpoint device 24 for transitory display via the end user application 25. The end user application 25 may display the summary list of messages as sorted chronologically, sorted by message priority, or sorted by other message characteristics identified by the host system 10. In various embodiments, the end user application 25 may display flagged messages, non-flagged messages, or a combination thereof. In circumstances of a combined display, the end user application may display flagged messages with more prominence than non-flagged messages for easier identification of important message content.

The method 200 then proceeds to step 222 by monitoring for user feedback regarding the message flag categorization. In various embodiments, a user may override the flagging of messages as described in step 221. For example, a user may choose to flag a non-flagged message, thereby identifying it as important, or may choose to de-flag a flagged message, thereby identifying it as unimportant. If the host system 10 receives user feedback in this manner, the host system 10 may analyze the digest algorithm used to perform the analysis and modify the algorithm to improve the sensitivity and specificity of future results incorporating said algorithm (step 223). In an embodiment, the host system 10 may adjust the relative weights of the specified characteristic variables to improve flagging accuracy. The host system 10 may employ a machine learning engine effective to improve the digest algorithm according to user feedback.

If a user requests a patient safety analysis (PSA) report for a patient, the method 200 proceeds to step 224 by forwarding the PSA report request from the user's endpoint device 24 to the host system. The host system 10 may load from the algorithm database 20 a PSA algorithm that instructs the host system 10 in performing the patient safety analysis.

The method 200 continues in step 225 by collecting patient data to be processed and displayed in the patient safety analysis report. In various embodiments, the host system 10 requests patient data from the electronic medical records system (16) and message data from the message database (19). The host system 10 may request patient data including patient diagnoses, patient status, treating clinicians, and care-related events associated with the patient. The host system 10 may request message data including message content, total number of messages, the time at which messages were sent, and healthcare provider participation in messages.

Upon receiving the requested data, the host system 10 analyzes the data in accordance with the PSA algorithm (step 226). Specifically, the host system 10 may calculate the likelihood of that a communications breakdown resulting in medical error will occur. The result of this analysis may be streamed to the user's endpoint device 24 for display via the end user application 25.

If a user requests patient analytics, the method 200 proceeds to step 227 by forwarding the analytics request from the user's endpoint device 24 to the host system. The host system 10 may load from the algorithm database 20 an analytics algorithm that instructs the host system 10 in performing the analytics.

The method 200 continues in step 228 wherein the host system 10 requests patient data from the electronic medical records system 16 and message data associated with the patient from the message database 19.

The method 200 proceeds to step 229 wherein the host system 10 may analyze the data in accordance with an analytics algorithm stored on the algorithm database 30. In various embodiments, the host system 10 may perform various data transformations including identifying the number of unanswered messages associated with the patient, graphing message volume over time, summarizing message volume by type over time, and comparing the volume of messages associated with the patient to a benchmark volume. The benchmark volume may be, for example, an ideal volume, an average volume, or another useful volume for comparison in determining the likelihood of a medical error occurring due to a breakdown in communication. In certain embodiments, benchmark comparisons may be made according to factors shared between other patients including the patient's first listed diagnosis, the unit in which the patient is located, the healthcare provider of the patient, and the day of hospitalization of the patient. In an additional embodiment, the data transformations may be made for more than one patient or healthcare provider so as to identify general trends and outlier data indicating a higher likelihood of medical error occurring. The data transformations may be streamed to the user's endpoint device 24 for viewing via the end user application 25.

Figure 3:
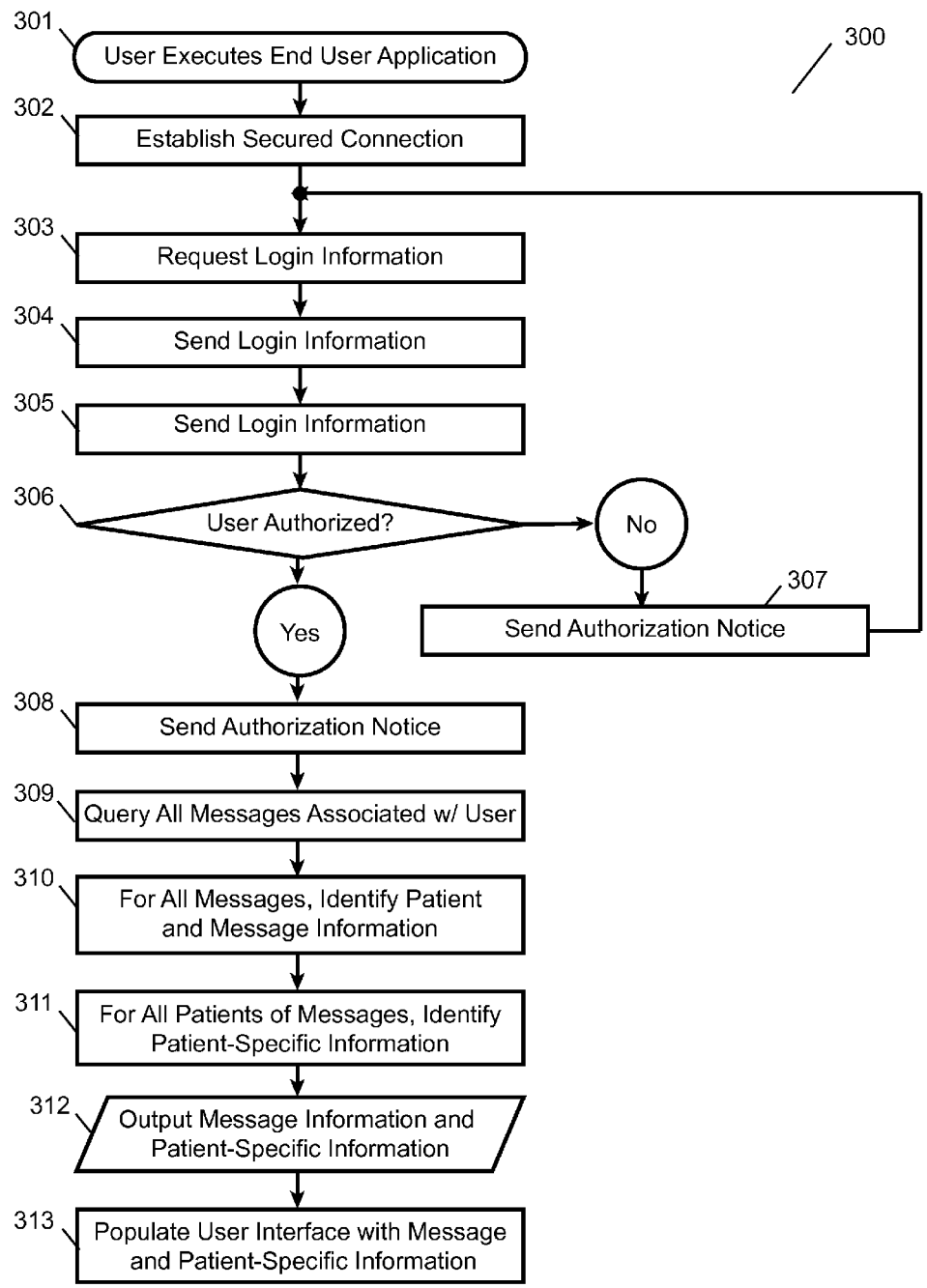
FIG. 3 is a flowchart representing an embodiment of a login process according to the present invention.

FIG. 3 demonstrates an example methodology for securely authenticating a user login from an endpoint device. The method 300 begins at a first step 301 when a user executes the end user application 25 upon the endpoint device 24. The endpoint device 24 connects to the host system 10 using a secured connection (step 302). In one embodiment the secured connection may include a secure socket layer (SSL) connection to an external API 23 residing on a DMZ host 28 communicatively coupled to the host system 10. In certain embodiments, connections may be made according to but not limited to WebSockets protocols, Server-side events protocols, or AJAX long-polling protocols. Once a secured connection has been established, the method 300 continues in step 303 by sending a request for login information over the secured connection to the endpoint device 24. In one embodiment, login information may include a user name and password associated with the user name.

The method 300 continues in step 304 by receiving the requested login information from the endpoint device 24 through the secured connection. The method 300 continues in step 305 by sending the received login information to an authentication server. In one embodiment, the authentication server may be a third-party Single Sign-On Authentication server associated with multiple healthcare login systems. In an alternative embodiment, the authentication server may be a subroutine of the host system 10.

The method 300 continues in step 306 by determining whether the endpoint device 24 is authorized to access the host system 10 by comparing the login information received to credential data associated with the authentication server. In one embodiment, successful authentication may allow the endpoint device access to additional medical systems or databases not directly associated with the host system. If authorization fails, the method 300 continues to step 307, by sending a rejection notice to the endpoint device and requests login information again according to step 303. Alternatively, if authorization is granted, the method 300 proceeds to step 308, whereupon notice of authorization is sent to the endpoint device 24.

The method 300 continues at step 309 by querying for messages associated with the user. In certain embodiments, the messages queried may represent all messages associated with a user or alternatively may represent only a subset of total messages associated with the user. In step 310, the patient associated with each message and the information associated with each message may be determined. In one embodiment, the information associated with each message may include the patient name, the message subject, the message read status, the message priority, and the message content for each message. The method 300 continues in step 311 by requesting patient-specific information for each patient identified in step 310. In one embodiment, the patient-specific information may be queried from an Emergency Medical Record system. Patient-specific information may include but is not necessarily limited to patient's demographic information, patient's medical diagnoses, patient's medical care status, clinicians treating the patient, and care-related events with which the patient is associated.

In step 312, the message information obtained step 310 and the patient information obtained step 311 is outputted to the authorized endpoint device. In one embodiment, the data is streamed in a transitory state effective to prevent any of the message information from step 310 or medical information from step 311 from persisting on an endpoint memory 26 subsequent to termination of the login pursuant to the method 300. For example, the message information and patient information may be streamed from the host system to an external API to which the endpoint device connects for the duration of the authorized login session according to the method 300, and upon termination of the method 300, the endpoint device deletes all temporary files associated with the viewing of the message information and patient information.

The method 300 continues in step 313 by populating a graphical user interface viewable by the endpoint device with the message information and patient information. In one embodiment, the graphical user interface may arrange the message information chronologically as a list of messages. In another embodiment, the graphical user interface may arrange the message information according to a list of patients with which the message information is associated. In certain embodiments, the graphical user interface may include user-selectable message lists having multiple methods of configuration, user-executable functions, and user-viewable message data.

Figure 4:
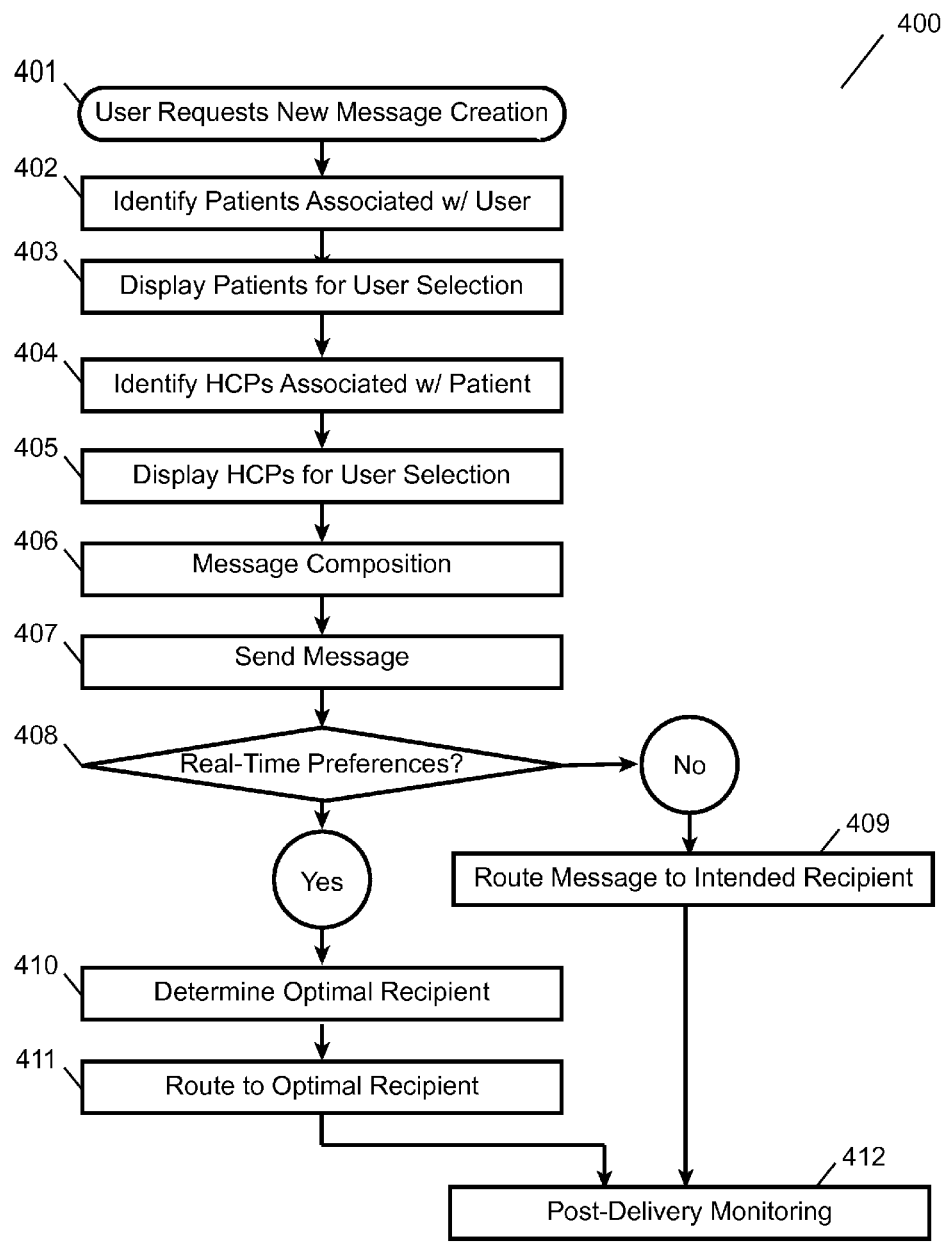
FIG. 4 is a flowchart representing a series of steps for routing a message to an optimal recipient according to the present invention.

FIG. 4 is an example methodology for routing a message to an optimal recipient. The method 400 begins at step 401 when a user requests from an endpoint device 24 for a new message to be created. Upon receiving the request for a new message, the host system 10 identifies medical patients associated with a user (step 402). In certain embodiments, medical patients may be associated with a user where the user is a clinician for the patient. The method 400 continues in step 403 by displaying to the user a list of the identified patients. In certain embodiments, the user may choose one or more of the patients to whom the message will pertain. Additionally, in certain embodiments, more than one list of patients may be displayed. In an embodiment, the user may choose instead to have all patients displayed including those not determined in step 402 to be associated with the user. In another embodiment, the user may search for a specific patient wherein the host system 10 will display a list of patients associated with the user's search terms.

Once the user selects the patient or patients with whom the message is associated, the method 400 proceeds to step 405 by displaying a list of healthcare providers associated with the patient. In certain embodiments, the user may choose one or more of the healthcare providers as intended recipients of the message. Additionally, in certain embodiments, more than one list of healthcare providers may be displayed. In an embodiment, the user may choose to select a healthcare provider not among the list of healthcare providers associated with the patient. Selecting a healthcare provider in this manner may therefore associate the selected healthcare provider with the patient.

The method 400 continues in step 406 whereby the user composes a message. In one embodiment, the user may compose a text message through a graphical user interface. In alternative embodiments, the user may compose a voice message and/or a picture message. In another embodiment, the user may choose a priority level for the message. The priority level may be chosen from predetermined priorities such as "STAT," "ASAP," "When Possible," or "FYI."

The host system then determines whether the intended recipient has routing preferences (step 408). In an embodiment, an intended recipient's routing preferences are algorithms that define routing behavior for the message given certain circumstances. For example, a routing preference may specify to route the message to an alternative recipient if the recipient is within, or alternatively not within, a certain geospatial location. In certain embodiments, routing preferences may be defined according to the date, the time of day, and the geospatial location of the user and/or the user's endpoint device 24. For example, a recipient's routing preferences may declare that incoming messages should be routed to another recipient, such as the physician on call, if the user's endpoint device 24 is physically located off hospital premises as determined by GPS coordinates, or as determined by visibility of or connectivity to certain WiFi networks, or as determined by visibility or connectivity to certain cellular network towers, or as determined by a combination thereof. In another example, a recipient's routing preferences may declare that incoming messages should be routed to another recipient if the message has been sent at a specific date or time, such as at 2:00 a.m. or on weekends. In a third example, a recipient's routing preferences may declare that only messages of a certain priority should be routed to the recipient and that messages below the specified priority threshold should be routed to another recipient.

In another embodiment, the routing preferences may be defined according to whether one or more wireless communications networks are visible to the endpoint device 24 associated with the intended recipient. In additional embodiments, a recipient's routing preferences for receiving messages may be defined by the recipient. Alternatively, or in combination therewith, a recipient's routing preferences may be automatically determined through analysis of third-party systems in communication with the host system 10. For example, a recipient's routing preferences may be defined according to the recipient's hospital calendar, task list, or on-call schedule. In another example, a recipient's routing preferences may be defined according to forwarding protocols as specified by the call systems databases, such as forwarding messages to a specific individual or clinic or practice, or to an individual or clinic or practice on call for the recipient, or to a service line.

If the intended recipient does not have any routing preferences defined, then the method 400 proceeds to step 409 by routing the message to the intended recipient. In an embodiment, routing of the message associates the message with the intended recipient so that the intended recipient has visibility to the message hosted on the message database 19. In an additional embodiment, the intended recipient is notified upon receipt of the message by direct notification through the system or by push notification through a third-party system. Examples of third-party push notification systems include but are not limited to Apple Push Notification, Android Push Notification, Parse, and Urban Airship. The method then proceeds to step 412 further defined hereinafter.

Alternatively, if the intended recipient does have routing preferences defined, then the method 400 proceeds to step 410 wherein an optimal recipient is determined. In one embodiment, the optimal recipient is determined according to the routing preferences of the intended recipient. The intended recipient's routing preferences may specify to route the message to a specific individual, group, or practice. The intended recipient's routing preferences may specify to route the message to a general individual, group, or practice, whereby the host system 10 may determine which specific recipient associated with the individual, group, or practice is optimal for receiving the message. In an embodiment, routing of the message associates the message with the optimal recipient so that the optimal recipient has visibility to the message hosted on the message database 19. In certain embodiments, the message may also be associated with and/or visible to the intended recipient as well as the optimal recipient. In an additional embodiment, the optimal recipient is notified upon receipt of the message by direct notification through the system or by push notification through a third-party system. In certain embodiments, the intended recipient may also receive the same or similar notification. Examples of third-party push notification systems include but are not limited to Apple Push Notification, Android Push Notification, Parse, and Urban Airship. The method then proceeds to step 412 further defined hereinafter.

Once the message has been routed to the intended and/or optimal recipient, the method 400 proceeds to step 412 by engaging in post-delivery monitoring of the message. In various embodiments, post-delivery monitoring includes determination of whether the message has been read by the intended and/or optimal recipient and whether the intended and/or optimal recipient has responded to the message. Response to the message may include a subsequent message sent in reply or may include performance of a specific action. For example, a recipient may respond to a message by scheduling an event associated with a certain patient as determined by the host system 10. An example of a methodology for engaging in post-delivery message monitoring is further provided in FIG. 5.

Figure 5:
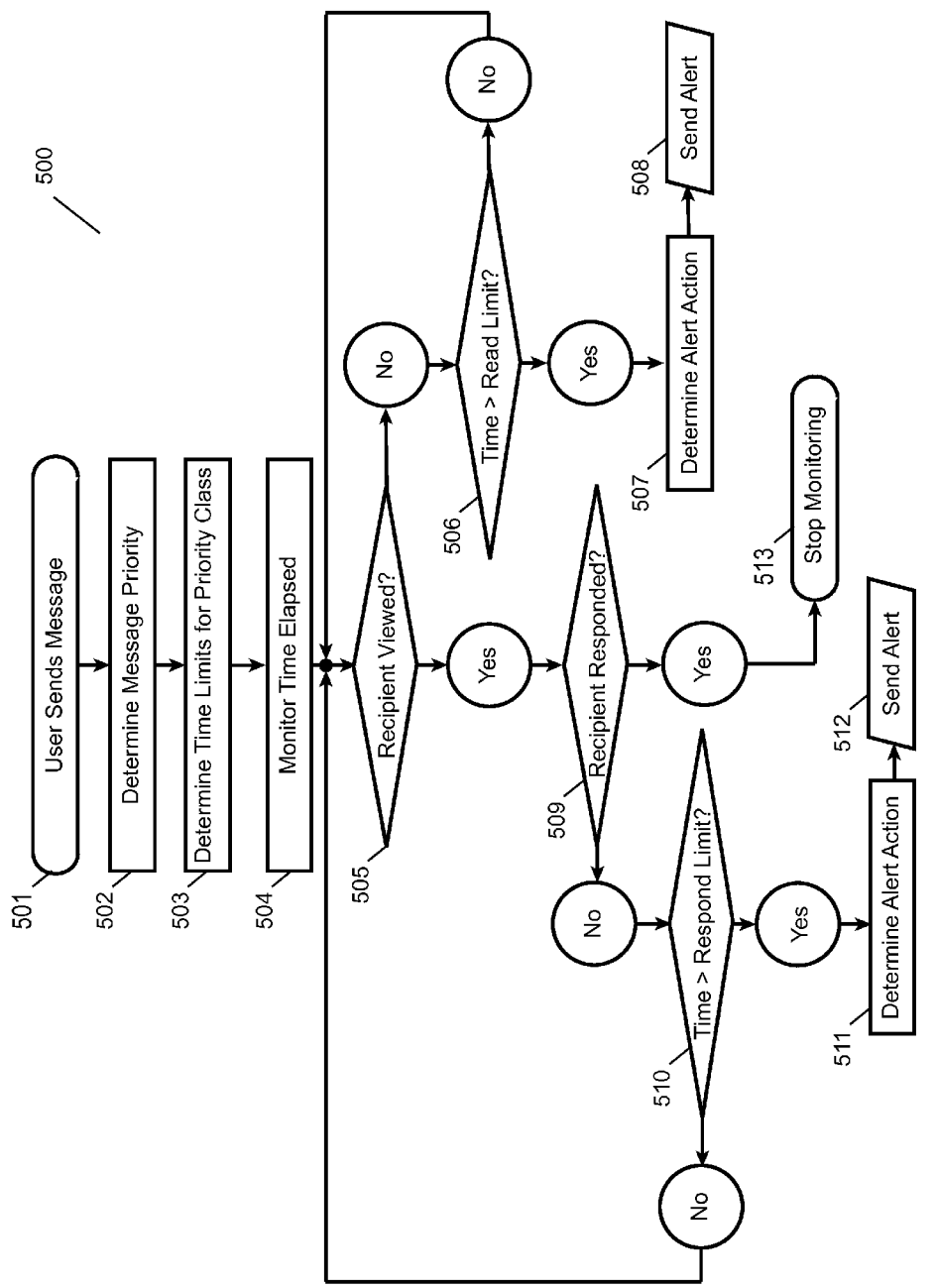
FIG. 5 is a flowchart representing a series of steps for monitoring the risk of communications breakdown according to the present invention.

FIG. 5 is an example of a methodology for monitoring the risk of communications breakdown. The method 500 begins at step 501 when a user sends a message to a recipient. In one embodiment, the message is associated with a recipient so that the recipient may view the message from an endpoint device 24. The method 500 continues in step 502 wherein the priority of the message is determined. In various embodiments, the user who composed the message may specify the priority of the message. The priority may be selected from a list of pre-defined priority statuses. For example, a user may choose a priority level for a message of "STAT," "ASAP," "When Possible," or "FYI." Alternatively, the priority of the message may be determined by the host system 10 through natural language analysis of the message content. The host system may determine the priority of a message based on the presence of certain keywords within the message content. For example, detection of the phrase "patient is coding" or "pt coding" may, according to one or more natural language processing algorithms, warrant the host system to determine a message priority of "STAT." In an alternative embodiment, the message priority may be defined as null with no associated value.

Once the message priority has been determined, one or more time limits are determined according to the message priority level (step 503). In various embodiments, one or more priority levels may have one or more associated time limits each for the maximum time the message may go unread or for the maximum time to which a message may go without response. A higher priority level may have a shorter time limit in which a message must be read or responded to than compared to a lower priority level. A lower priority level may have a longer associated time limit or alternatively no associated time limit. For example, a message with a high priority of "STAT" may have a response time limit of 2 minutes, whereas a message with a low priority of "FYI" may have no response time limit and a read time limit of 24 hours.

The method 500 continues in step 504 wherein the host system 10 monitors the time elapsed since the message has been sent to the recipient. During this monitoring, the host system performs step 505 by determining whether or not the recipient has viewed the message. In one embodiment, the host system 10 may determine that the recipient has viewed the message where the recipient has selected, clicked on, or otherwise interacted with the message as viewed through the end user application 25 on the recipient's endpoint device 24.

If the recipient has not viewed the message, the method 500 proceeds to step 506 by comparing the time elapsed since the message was sent to the read time limit associated with the message priority level as determined in step 503 above. In one embodiment, the determined read time limit for the specified priority level may be null, wherein the host system 10 may either continue monitoring the read status of the message or may cease monitoring the read status of the message. If the time elapsed has not exceeded the read limit, then the method 500 may continue to monitor the time elapsed as further described above in step 504. Alternatively, if the time elapsed has exceeded the read limit, the host system 10 may determine an appropriate alert action according to one or more algorithms 30 stored in the algorithms database 20. In certain embodiments, the algorithm 30 may specify to send an e-mail to a user, place an automated phone call to a user, or send a notification to a user. In further embodiments, the user may be predetermined according to the algorithm 30 or alternatively determined and selected from a connected call systems database 17. In further embodiments, a notification may include direct notification through the system or by push notification through a third-party system. Examples of third-party push notification systems include but are not limited to Apple Push Notification, Android Push Notification, Parse, and Urban Airship.

Once an appropriate alert action has been determined, the method 500 proceeds to step 508 wherein an alert is sent according to the alert action determined in step 507. In one embodiment, the host system 10 may continue to monitor the message according to step 504 following sending the alert in order to determine whether to send subsequent alerts. For example, if the time elapsed exceeds a second read limit, a second alert of an escalated priority may be triggered. For example, if a recipient fails to read a message in a determined amount of time following generation of an initial alert, a subsequent alert may be sent to the recipient or to a physician on call so as to prevent the occurrence of a medical error.

If the recipient has viewed the message, the method 500 proceeds to step 509 by determining whether the recipient has responded to the message. In various embodiments, the host system may determine that the recipient has responded to the message by composing a new message associated with and in response to the first message. In another embodiment, the host system 10 may determine that the recipient has responded to the message by determining that the recipient has performed a subsequent action such as scheduling an event, filling a prescription, or admitting a patient.

If the recipient has not responded to the message, the method 500 proceeds to step 510 by comparing the time elapsed since the message was sent to the response time limit as associated with the message priority level as determined in step 503 above. In one embodiment, the determined response time limit for the specified priority level may be null, wherein the host system 10 may either continue monitoring the response status of the message or may cease monitoring the read status of the message. If the time elapsed has not exceeded the response limit, then the method 500 may continue to monitor the time elapsed as further described above in step 504. Alternatively, if the time elapsed has exceeded the response limit, the host system 10 may determine an appropriate alert action according to one or more algorithms 30 stored in the algorithms database 20. In certain embodiments, the algorithm 30 may specify to send an e-mail to a user, place an automated phone call to a user, or send a notification to a user. In further embodiments, the user may be predetermined according to the algorithm 30 or alternatively determined and selected from a connected call systems database 17. In further embodiments, a notification may include direct notification through the system or by push notification through a third-party system. Examples of third-party push notification systems include but are not limited to Apple Push Notification, Android Push Notification, Parse, and Urban Airship.

Once an appropriate alert action has been determined, the method 500 proceeds to step 511 wherein an alert is sent according to the alert action determined in step 507. In one embodiment, the host system 10 may continue to monitor the message according to step 504 following sending the alert in order to determine whether to send subsequent alerts. For example, if the time elapsed exceeds a second response limit, a second alert of an escalated priority may be triggered. For example, if a recipient fails to respond to a message in a determined amount of time following generation of an initial alert, a subsequent alert may be sent to the recipient or to a physician on call so as to prevent the occurrence of a medical error.

If the recipient has responded to the message, the method 500 may conclude at step 513 by ceasing the monitoring activities as specified above in step 504. In an alternative embodiment, the host system 10 may continue to monitor the message for additional responses for purposes of determining message analytics.

Figure 6:
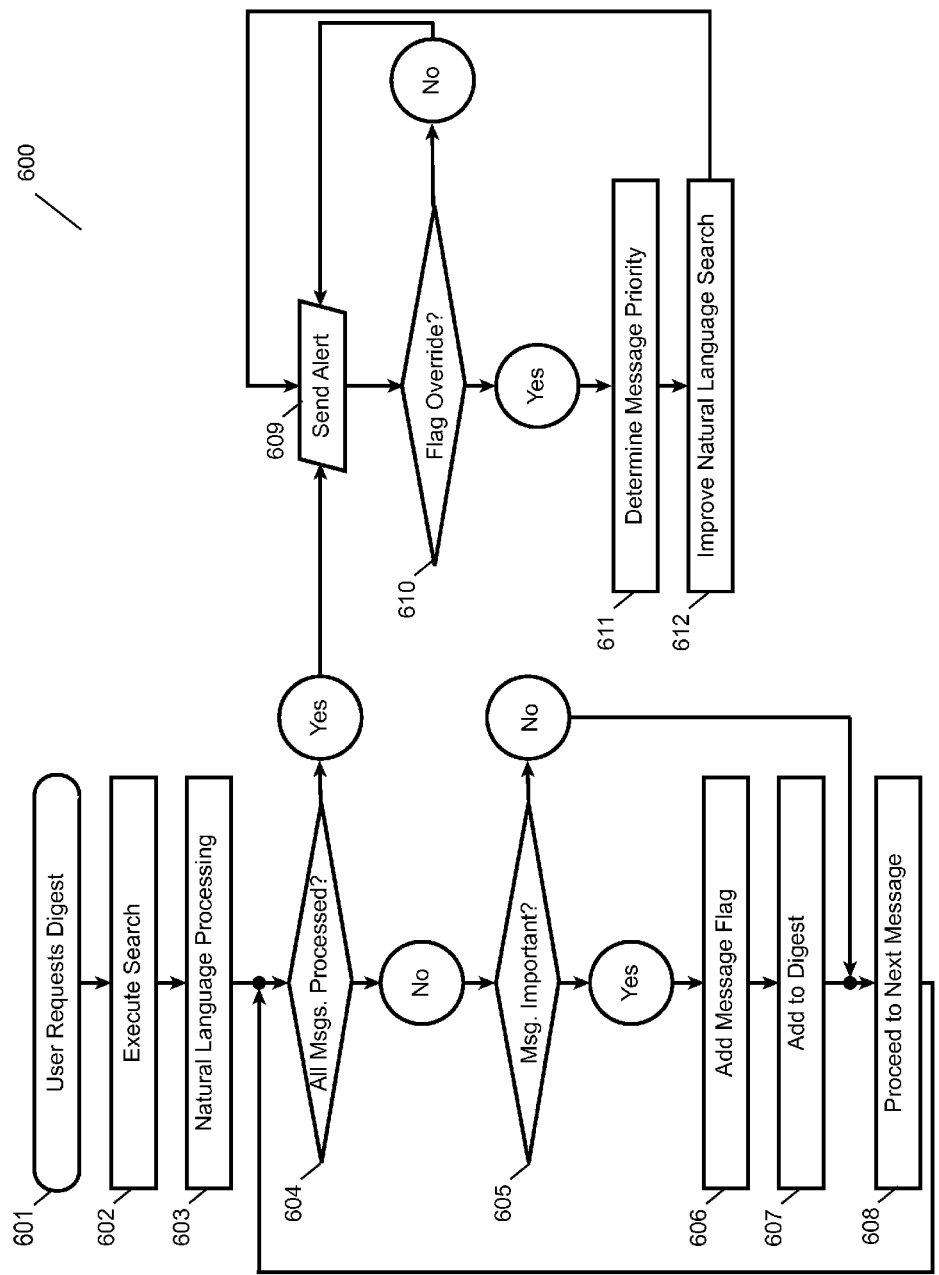
FIG. 6 is a flowchart representing a series of steps for creating a patient digest from associated messages according to the present invention.

FIG. 6 is an example of a methodology for creating a digest of messages associated with a patient. The method 600 begins at step 601 when a user requests a digest and the host system 10 receives such request. In one embodiment, a user may request a digest by selecting a digest option within the end user application 25 upon the user's endpoint device 24. In an alternative embodiment, the digest may be generated automatically or periodically and without user input.

Once the host system 10 has received a digest request, the host system 10 may execute a search for all messages 27 stored on the message database 19 and associated with the patient for whom the digest was requested (step 602). In various embodiments, this search may be performed by implementing a digest algorithm from the plurality of algorithms 30 stored upon the algorithm database 20. When all associated messages have been queried, the method 600 proceeds to step 603 by applying a natural language processing algorithm to the messages 27 and associated message content 29.

The method 600 continues in step 604 by analyzing whether all of the associated messages have been analyzed with the natural language processing. If not all associated messages have been analyzed, the method continues to step 605 wherein the host system 10 determines the importance of individual messages and content of messages by processing message characteristics. Message characteristics may include the message priority, the time the message was sent, the time elapsed since the message has been sent, the recipients of the message, and the content of the message. If the host system 10 determines that the message is important, it will add a flag to the message (step 606). In various embodiments, the flag may be visible in the end user application 25 in viewing the digest summary or the message directly. The flagged message is subsequently added to the digest summary (step 607), and the host system 10 then proceeds to the next message for processing (step 608). Alternatively, if the message is not deemed important, no flag is added to the message, and the host system 10 proceeds to the next message as per step 608.

When all associated messages have been processed according to the natural language algorithm, the method 600 proceeds to step 609 wherein the digest summary is displayed, representing a collection of the most important messages associated with the patient. In various embodiments, the digest summary may be displayed as a graphical user interface upon the end user application 25 populated by the flagged message data as determined in step 606. The digest summary may be displayed as a list of flagged messages only or alternatively as a mixed list of flagged messages and non-flagged messages wherein the flagged messages have higher visual prominence so as to distinguish them to the user. In an embodiment, the digest summary may be accessible to users not associated with the patient. For example, a nurse, doctor, or health care provider on rotation not otherwise directly associated with a certain patient may be able to request and view a digest for that patient under his or her immediate care.

The method 600 continues in step 610 by determining whether a flag override has occurred. In various embodiments, the initial determination of a message flag according to step 606 may be overridden by the user. For example, a user may determine that message flagged as important should not be flagged as important, and may remove the flag from the message, or alternatively may determine that an non-flagged message deemed unimportant is important and should be flagged. In certain embodiments, a user may override the initial determination of a message flag according to step 606 by selecting or deselecting the message flag within the message list interface or digest summary interface of the end user application.

If a user overrides a message flag in this manner, the method 600 proceeds to step 611 wherein the host system 10 toggles the message flag. In various embodiments, the toggle determination is Boolean, wherein a user may turn a flag for a message off or on. The method 600 then proceeds to step 612, wherein the host system 10 analyzes the natural language processing algorithm to determine how the natural language processing algorithm's sensitivity and specificity may be improved to ensure greater accuracy with future determinations of message importance. In one embodiment, the host system 10 may improve the natural language processing algorithm automatically through application of a machine learning engine or by adjusting the relative weight of the variables used to make the determination of message importance.

Figure 7:
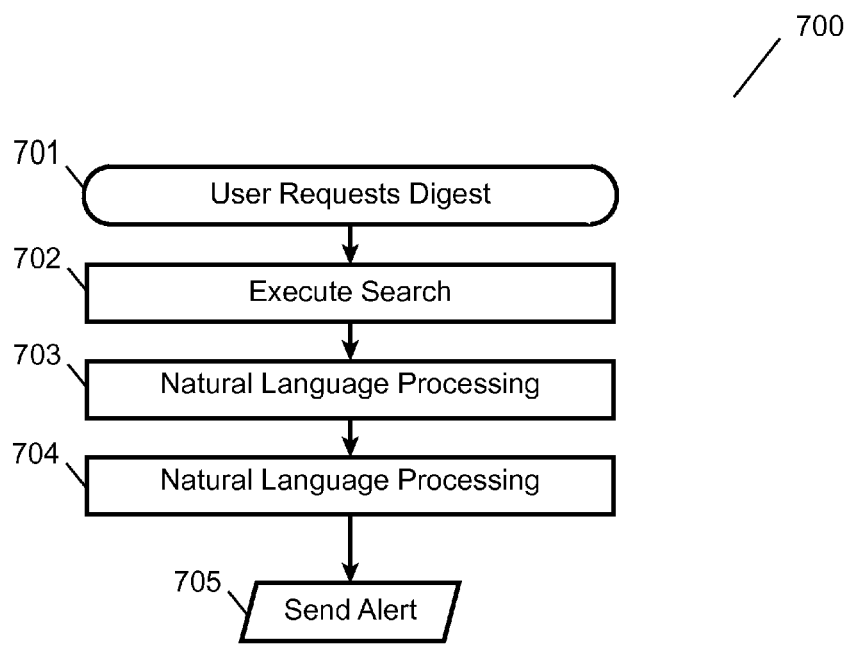
FIG. 7 is a flowchart representing a series of steps for creating a patient safety analysis according to the present invention.

FIG. 7 is an example of a methodology for creating a patient safety analysis report associated with a patient. The method 700 begins at step 701 when a user requests a patient safety analysis (PSA) report and the host system 10 receives such request. In one embodiment, a user may request a PSA report by selecting a PSA report option within the end user application 25 upon the user's endpoint device 24. In an alternative embodiment, the PSA report may be generated automatically or periodically and without user input.

Once the host system 10 has received a PSA report request, the method 700 proceeds to step 702 by requesting patient information. In various embodiments, patient information may be requested from third-party databases 15 such as the electronic medical records database 16. Patient information may include patient demographics, patient diagnoses, patient status, clinicians treating the patient, and care-related events associated with the patient such as hospitalizations, medical emergencies, transfers, medical procedures, and releases. Patient information may additionally include insurance status, total medications, number of procedures planned, and ability or inability to communicate due to mitigating circumstances such as medication or disease. In an embodiment, additional information may be collected pertaining to the patient's health care providers such as providers' years of experience, caseload, types of cases within caseload, and hours worked.

The method 700 proceeds to step 703 by requesting message information pertaining to the patient. In various embodiments, message information may be requested from the message database 19 wherein the messages 27 are associated with the patient 28. Message information may include message content, number of messages, priority of messages, the time at which the messages were sent, and clinician participation in messages. In an embodiment, additional information may be collected pertaining to the healthcare providers' messaging such as number of communications per day, number of patient handoffs, and types of handoffs regarding source and destination department.

The host system 10 may then apply a PSA algorithm to the collected patient information and message information (step 704). The PSA algorithm may predict a likelihood that a breakdown in communication resulting in a medical error will occur. In one embodiment, the PSA algorithm may be a logistic regression formula derived from data associated with the patient and the patient's health care providers. In such an embodiment, the logistic regression formula may be functionally related to a Boolean determination of prior medical error having occurred from a communication breakdown. In another embodiment, the weight of analyzed variables may be changed or altered according to the location of the patient, location of the healthcare facility, or location of the system deployment.

Figure 8:
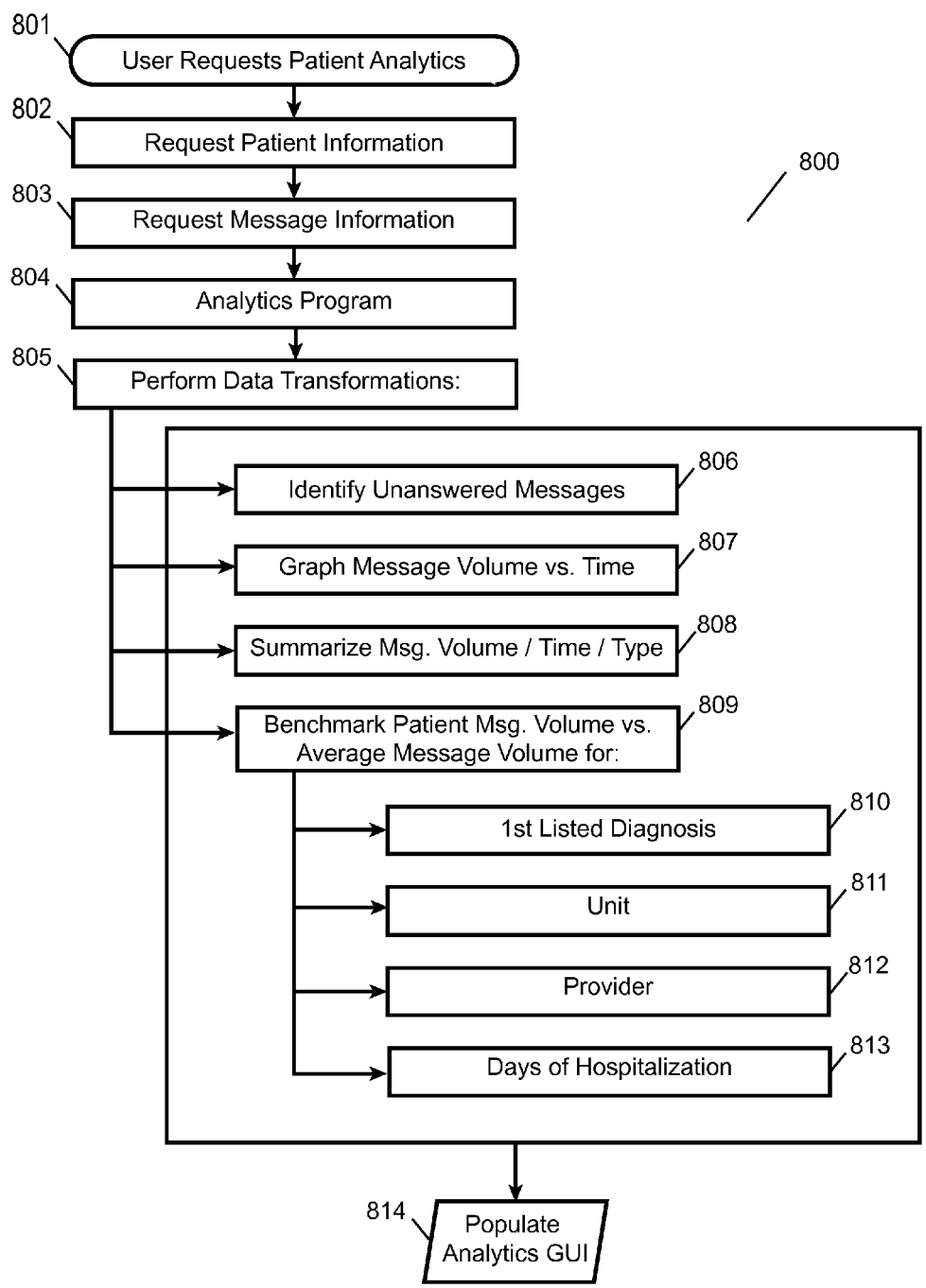
FIG. 8 is a flowchart representing a series of steps for creating patient analytics according to the present invention.

FIG. 8 is an example of a methodology for creating patient analytics report. The method 800 begins at step 801 when a user requests a patient analytics report and the host system 10 receives such request. In one embodiment, a user may request an analytics report by selecting an analytics report option within the end user application 25 upon the user's endpoint device 24. In an alternative embodiment, the analytics report may be generated automatically or periodically and without user input.

Once the host system 10 receives a request for a patient analytics report, the method continues at step 802 by requesting patient information. Patient information may include patient demographics, patient diagnoses, patient status, clinicians treating the patient, and care-related events associated with the patient such as hospitalizations, medical emergencies, transfers, medical procedures, and releases. Patient information may additionally include insurance status, total medications, number of procedures planned, and ability or inability to communicate due to mitigating circumstances such as medication or disease.

The method 800 proceeds to step 803 by requesting message information pertaining to the patient. In various embodiments, message information may be requested from the message database 19 wherein the messages 27 are associated with the patient 28. Message information may include message content, number of messages, priority of messages, the time at which the messages were sent, and clinician participation in messages.

The host system 10 may then apply an analytics algorithm to the collected patient information and message information (step 804). The analytics algorithm may then perform various data transformations to provide analytics upon the collected data. In various embodiments, the analytics algorithm may perform the steps of identifying what and how many of the messages associated with the patient are currently unanswered (step 806), graphing the volume of messages associated with the patient over a function of time (step 807), summarizing the volume of messages associated with the patient over a function of time based on message priority (step 808), and providing benchmarks regarding the number of messages associated with the patient against other patients in the hospital system (step 809). These steps may be performed individually or in any combination. In an additional embodiment, the host system 10 may further perform regressions of step 809 by providing messaging benchmarks based on patients who share the patient's first listed diagnosis (step 810), by providing messaging benchmarks based on patients within the same medical unit location as the analyzed patient (step 811), by providing messaging benchmarks based on patients who share the same health care provider as the analyzed patient (step 812), and by providing messaging benchmarks based on patient who have been hospitalized for the same number of days as the analyzed patient (step 813). In one embodiment, the benchmarks of steps 809 through 813 may provide a percentage of analyzed patient's message volume versus the average message volume of the control group over a specific period of time. In an additional embodiment, steps 809 through 813 may provide messaging benchmarks for a selected health care provider.

The method 800 then proceeds to step 814 by populating an analytics GUI with the transformed data. In one embodiment, the analytics GUI is displayed upon the end user application 25 of the user's endpoint device 24, the transformed data being streamed to the endpoint device in a non-persistent, transitory form. For example, the data may not persist on the endpoint device 24 after the session with the host system 10 is terminated. The transformed data may appear as one or more graphics color-coded to indicate threat metrics associated with a likelihood of communication breakdown resulting in medical error. In another embodiment, the analytics GUI may display transformed data for multiple patients within the same interface so as to allow the user to identify relative abnormalities that may represent a likelihood of communication breakdown resulting in medical error.

Referring now to FIGS. 1-8, in various embodiments the end user application 25 of the endpoint device 24 may generate a graphical user interface for the displaying of messages, message content, and related media for interacting with the host system 10. An example of such an embodiment may be described further with reference to FIGS. 9-12.

Figure 9:
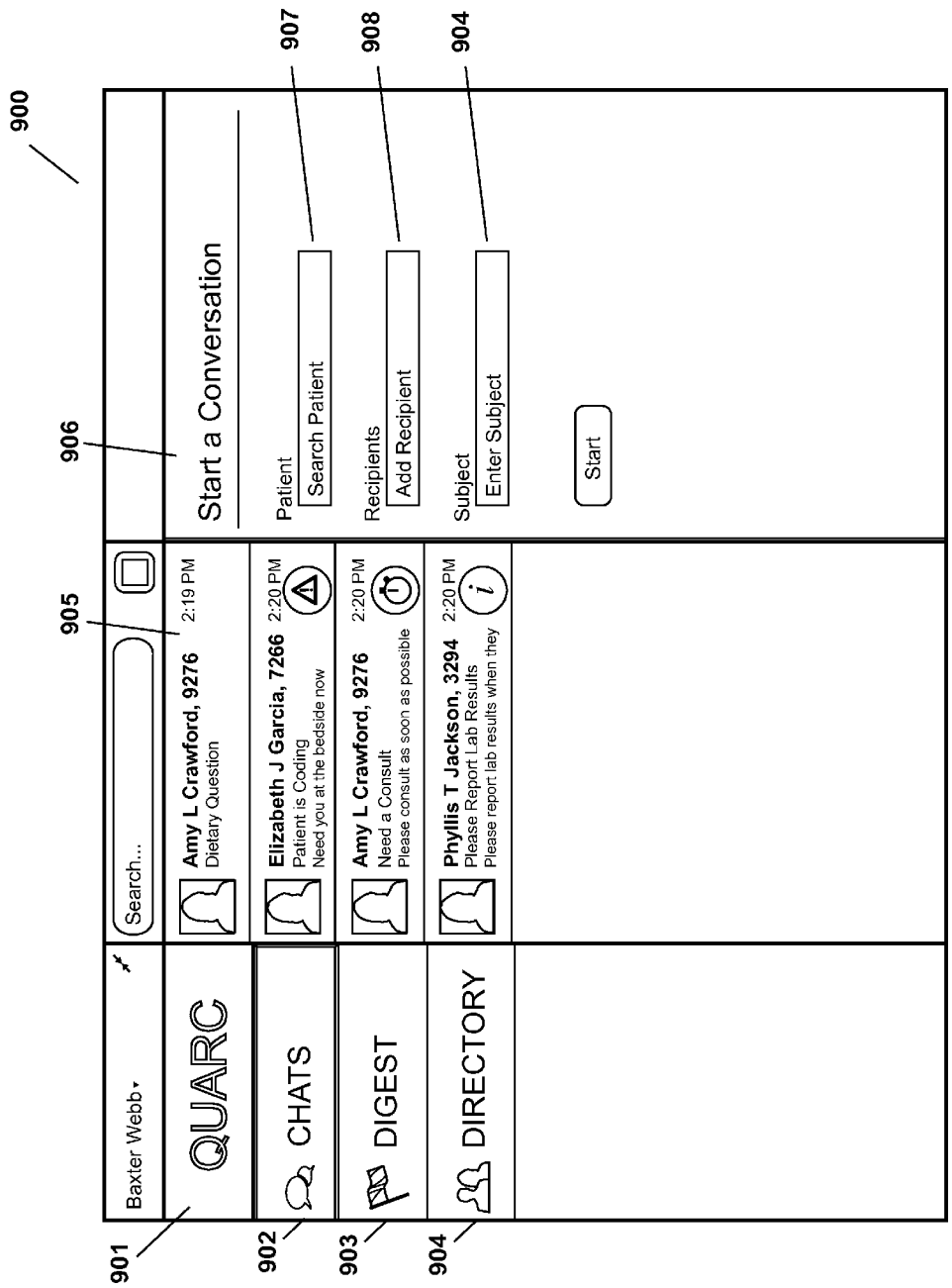
FIG. 9 is a modified screen shot representing an exemplary graphical user interface field according to the present invention.

FIG. 9 represents a default screen 900 whereby the user can perform various messaging functions. In this embodiment, a main menu 901 presents three selectable options whereby a user may choose to open a messaging interface 902, to request a patient digest 903, or open a directory of users and/or patients 904. A second portion of the screen is populated with a list of recently received messages 905. In this configuration, the messaging interface option 902 has been selected, resulting in a third portion of the screen being populated with a new message form 906. The user may choose a patient with whom the message will be associated 907, one or more recipients for the message 908, and a title subject for the message 909.

Figure 10:
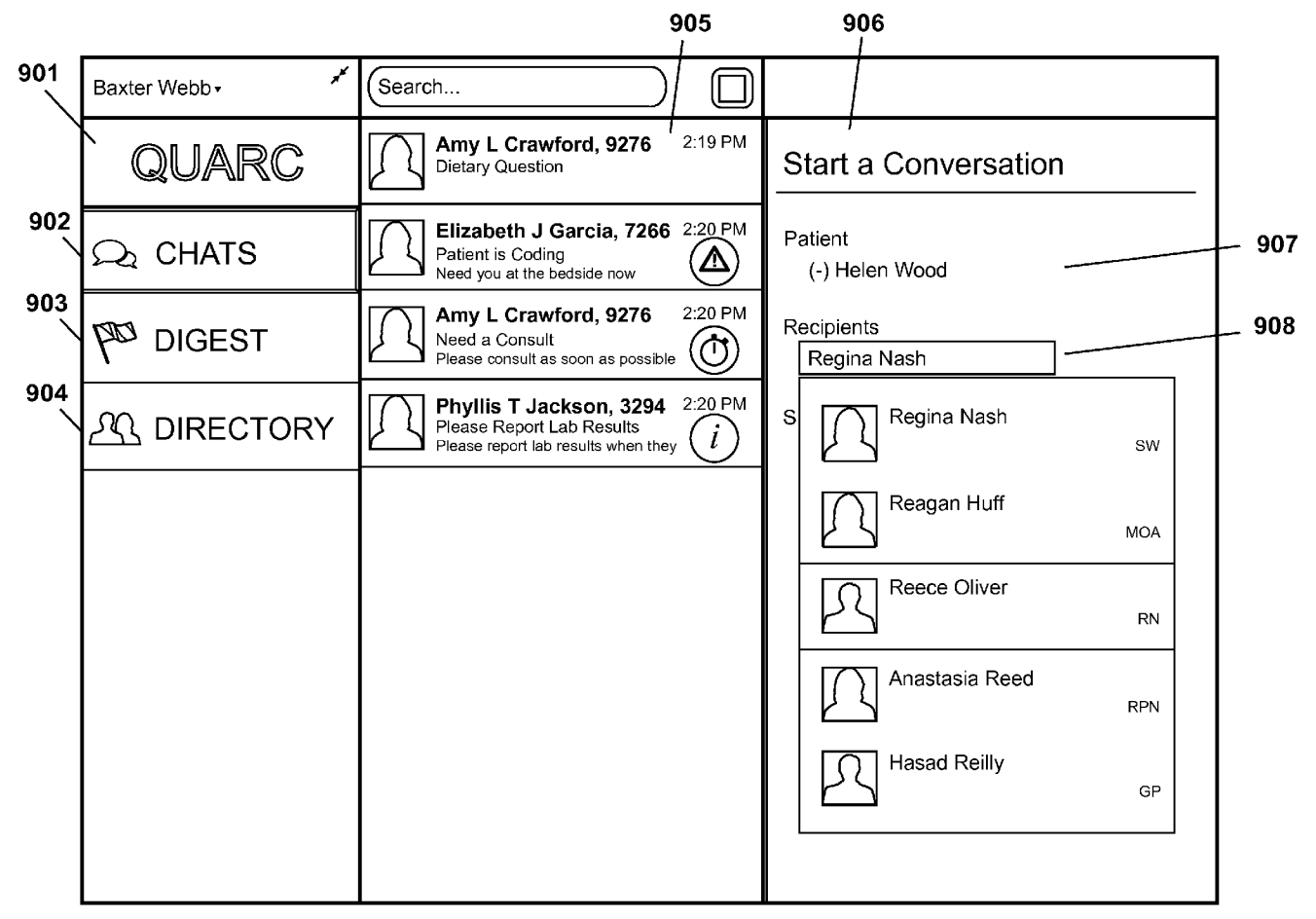

FIG. 10 represents a subsequent screen wherein the user has selected a patient 907 and may now select one or more recipients from an expanded list of recipients 908. In an embodiment, the expanded list of recipients 908 may preferably be populated only with healthcare providers associated with the selected patient 907.

Figure 11:
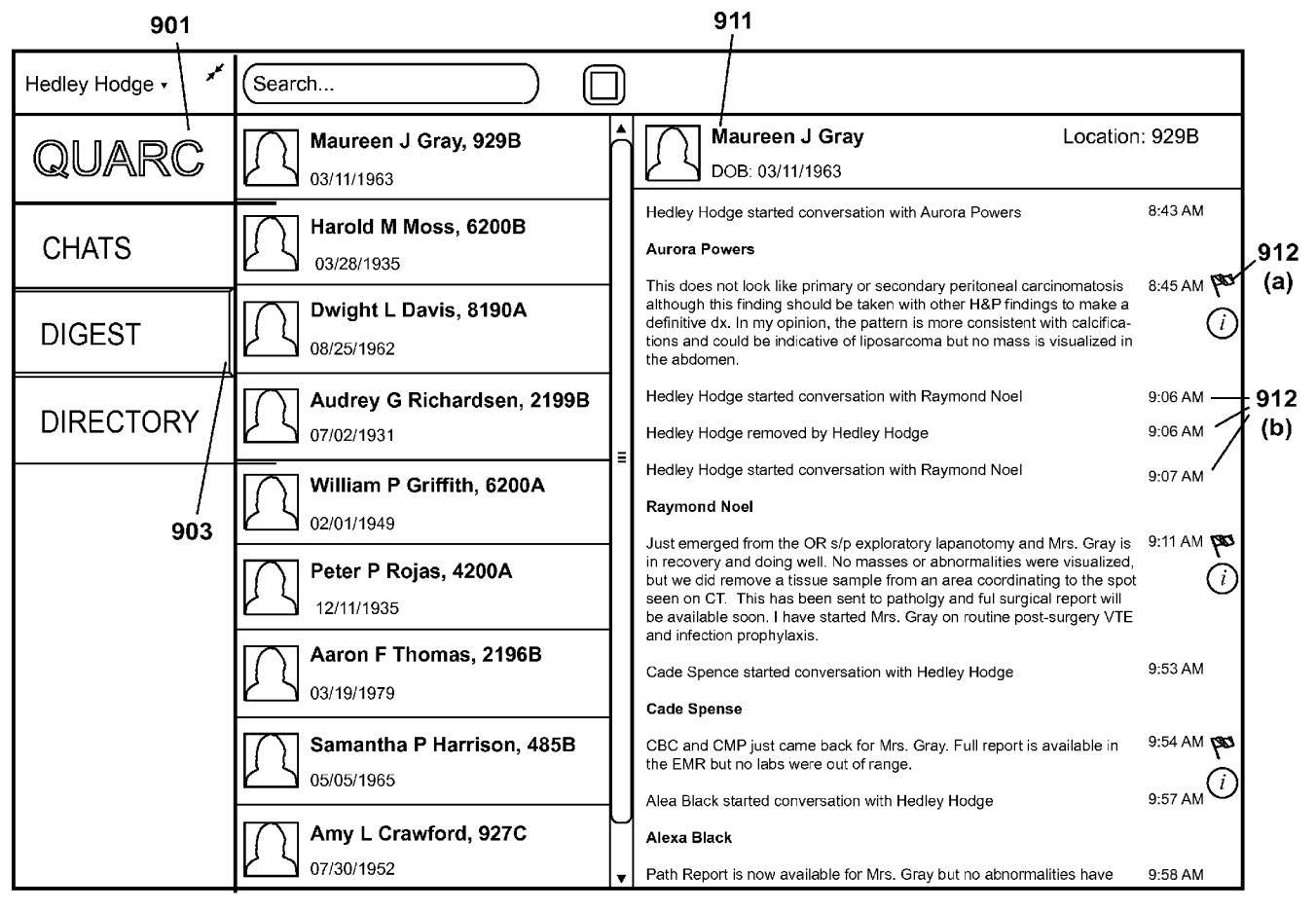

FIG. 11 represents a subsequent screenshot wherein the user has requested a patient digest 903 from the main menu 901. A second portion of the screen is populated with a list of patients 910 associated with the user. In this configuration, a patient has been selected, resulting in a third portion of the screen being populated with a digest summary 911 of messages associated with the patient. In this embodiment, the summary of messages is displayed as a chronological list wherein messages are flagged as important 912(a) or are not flagged as important 912(b).

Figure 12:
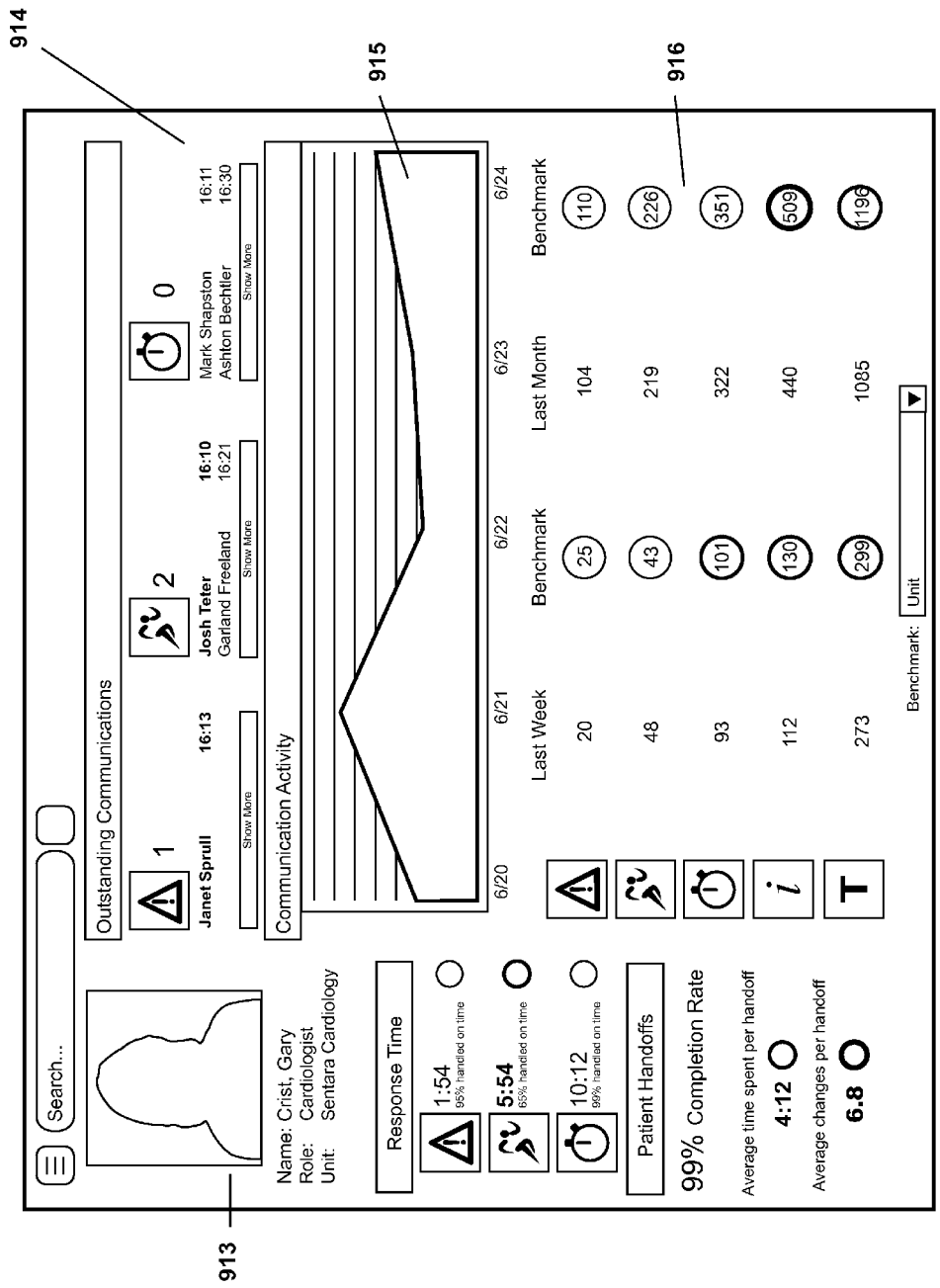
FIG. 12 is a modified screen shot representing a fourth exemplary graphical user interface field according to the present invention.

FIG. 12 represents a screenshot of a patient analytics report. In this embodiment, the name of the patient is displayed along with biographic and demographic information 913. Analytics pertaining to average response times for various message priorities is displayed with an average time of response, a percentage of timely responses, and an icon of a color corresponding to the percentage of timely responses. Additional information effective to indicate a likelihood of communication breakdown resulting in medical error may be displayed. In this configuration, additional information includes the number of messages unread or to which have not been responded separated into categories by priority 914, a graph of the volume of messages pertaining to the patient over a period of time 915, and the volume of message pertaining to the patient compared to an ideal benchmark as categorized by benchmark type, time period analyzed, and message priority 916.

The previous detailed description has been provided for the purposes of illustration and description. Thus, although there have been described particular embodiments of the present invention, it is not intended that such references be construed as limitations upon the scope of this invention except as set forth in the following claims.

What is claimed is:

1. A medical messaging server system comprising a non-transitory computer-readable medium having software residing thereon, the software executable by a processor to direct the performance of operations comprising:

enabling a user to create a message associated with a medical patient, the message comprising message content and an intended recipient selected from a plurality of healthcare providers;

algorithmically determining a priority value for the message based on an analysis of the message content and information associated with the patient;

determining an optimal recipient different from the intended recipient based on routing preferences comprising the priority for the message and a predicted likelihood of medical error resulting from communications breakdown with respect to the intended recipient;

delivering the message to the optimal recipient;

calculating a first value corresponding to a post-delivery status of the message, the value based in part on the priority value associated with the message; and generating an alert based on the first value exceeding a second value as a risk maximum threshold.

2. The server system of claim 1, an operation of predicting the likelihood of medical error resulting from communications breakdown comprising analyzing patient data associated with the patient from an electronic medical records system and message data associated with the patient from a message database functionally linked to the server with respect to associated benchmark values.

3. The server system of claim 2, the patient data comprising one or more of patient diagnoses, patient status, treating clinicians and care-related events.

4. The server system of claim 2, the message data comprising one or more of historical message content, a total number of messages, times at which the messages were sent, and healthcare provider participation in messages sent.

5. The server system of claim 4, the operation of predicting the likelihood of medical error resulting from communications breakdown further comprising comparing a total number of messages associated with the patient to a benchmark volume.

6. The server system of claim 5, the benchmark volume determined according to one or more of a first listed diagnosis of the patient, a healthcare provider for the patient and a day of hospitalization for the patient.

7. The server system of claim 1, the likelihood of medical error resulting from communications breakdown being predicted using a logistic regression formula derived from patient data and healthcare provider data, the formula further associated with a Boolean determination of prior medical error having occurred from a communication breakdown.

8. The server system of claim 1, the likelihood of medical error resulting from communications breakdown being further predicted based on a determined location of a messaging device associated with the intended recipient.

9. The server system of claim 8, the software further executable to determine the location of the messaging device associated with the intended recipient based on any one or more of GPS coordinates, a determined visibility of or connectivity with one or more defined WiFi networks, and a determined visibility of or connectivity with one or more defined cellular network towers.

10. The server system of claim 1, wherein the first value is calculated based on:
an elapsed time associated with the message, the elapsed time comprising a duration of time since the message was generated;
a read status associated with the message, the read status comprising information pertaining to whether the optimal recipient has viewed the message; and
a time limit associated with the read status.

11. The server system of claim 10, wherein the second value as a risk maximum threshold is determined by comparing the read status and the elapsed time against the time limit.

12. The server system of claim 10, wherein the time limit is determined according to the determined message priority associated with the message.

13. The server system of claim 1, the message routing preferences causing a message to be routed from the intended recipient to another recipient based on a determined location of a messaging device associated with the intended recipient being away from a location for the patient.

14. The server system of claim 13, the message routing preferences further causing a message to be routed from the intended recipient to another recipient based on a time of day and the priority value associated with the message.

15. The server system of claim 14, the message routing preferences defined according to predetermined forwarding protocols.

16. A medical messaging system comprising:
a perimeter communications network comprising a server interface for a plurality of user computing devices;
a server network communicatively linked to the perimeter network via a secure message bus, the server network comprising a processor, a data storage network and a non-transitory computer-readable medium having program instructions residing thereon, the instructions executable by the processor to direct the performance of operations comprising:
providing a user interface platform executable from the plurality of user computing devices, the user interface platform effective to
enable users to submit respective message routing preferences for storage in the data storage network, and
enable a first user to submit a messaging request associated with a medical patient, the messaging request defining a user as an intended recipient;
in response to the messaging request, identifying one or more users as healthcare providers associated with the patient;
generating a message associated with the patient, the message comprising patient-related content;
algorithmically determining a priority value for the message based on an analysis of the message content and information associated with the patient;
determining an actual recipient for the message from among the identified one or more healthcare providers based at least in part on message routing preferences associated with the intended recipient and comprising the priority for the message and a predicted likelihood of medical error resulting from communications breakdown with respect to the intended recipient;
delivering the message to the actual recipient;
applying a risk assessment algorithm effective to determine a first value corresponding to a post-delivery status of the message, the value based in part on the priority value associated with the message;
comparing the first value to a second value as a risk maximum threshold, wherein if the first value exceeds the second, further generating an alert associated with the patient to an alert recipient chosen from the one or more healthcare providers;
calculating messaging benchmarks associated with the patient based on expected messaging activity for each of one or more user-selectable benchmark criteria; and
user-selectably generating a graphical representation of the calculated benchmarks with respect to actual messaging activity associated with the patient, the graphical representation displayable on a respective user interface platform.

17. The medical messaging system of claim 16, an operation of predicting the likelihood of medical error resulting from communications breakdown comprising analyzing
patient data associated with the patient from an electronic medical records system, the patient data comprising one or more of patient diagnoses, patient status, treating clinicians and care-related events, and
message data associated with the patient from a message database functionally linked to the server with respect to associated benchmark values, the message data comprising one or more of historical message content, a total number of messages, times at which the messages were sent, and healthcare provider participation in messages sent.

18. The medical messaging system of claim 17, the operation of predicting the likelihood of medical error resulting from communications breakdown further comprising using a logistic regression formula derived from patient data and healthcare provider data, the formula further associated with a Boolean determination of prior medical error having occurred from a communication breakdown.

19. A method for reducing medical error resulting from communications breakdowns between healthcare providers, the method comprising:
- providing a user interface enabling a user to create a message associated with a medical patient, the message comprising message content and an intended recipient selected from a plurality of healthcare providers;
- algorithmically determining a priority value for the message based on an analysis of the message content and information associated with the patient;
- determining an optimal recipient different from the intended recipient based on routing preferences comprising the priority for the message and a predicted likelihood of medical error resulting from communications breakdown with respect to the intended recipient;
- delivering the message to the optimal recipient;
- calculating a first value corresponding to a post-delivery status of the message, the value based in part on the priority value associated with the message; and
- generating an alert based on the first value exceeding a second value as a risk maximum threshold.

20. The method of claim 19, wherein the likelihood of medical error resulting from communications breakdown is predicted using a logistic regression formula derived from patient data and healthcare provider data, the formula further associated with a Boolean determination of prior medical error having occurred from a communication breakdown.

\* \* \* \* \*